(12) United States Patent
Gu

(10) Patent No.: US 10,024,833 B2
(45) Date of Patent: Jul. 17, 2018

(54) QUALITY CONTROL OF DAIRY PRODUCTS USING CHROMATIC PROFILES

(71) Applicant: Empire Technology Development LLC, Wilmington, DE (US)

(72) Inventor: Yansong Gu, Bellevue, WA (US)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 0 days.

(21) Appl. No.: 15/501,402

(22) PCT Filed: Aug. 8, 2014

(86) PCT No.: PCT/US2014/050393
§ 371 (c)(1),
(2) Date: Feb. 2, 2017

(87) PCT Pub. No.: WO2016/022152
PCT Pub. Date: Feb. 11, 2016

(65) Prior Publication Data
US 2017/0227511 A1    Aug. 10, 2017

(51) Int. Cl.
*G01J 3/46* (2006.01)
*G01N 33/06* (2006.01)
*G01N 21/25* (2006.01)

(52) U.S. Cl.
CPC .......... *G01N 33/06* (2013.01); *G01N 21/255* (2013.01); *G01N 2201/0627* (2013.01); *G01N 2201/1293* (2013.01)

(58) Field of Classification Search
CPC . G01J 3/02; G01J 3/46; G01N 21/255; G01N 33/06
See application file for complete search history.

(56) References Cited

U.S. PATENT DOCUMENTS

| 5,137,364 A | 8/1992 | McCarthy |
| 5,844,680 A | 12/1998 | Sperling |
| 7,996,173 B2 | 8/2011 | Schowengerdt et al. |
| 8,076,630 B2 | 12/2011 | Schowengerdt et al. |
| 8,638,441 B2 | 1/2014 | Egan et al. |
| 2002/0154311 A1* | 10/2002 | Ivarsson ................ G01N 21/59 356/437 |
| 2005/0046850 A1 | 3/2005 | Chow |

(Continued)

FOREIGN PATENT DOCUMENTS

DE            4202822 A1     8/1992

OTHER PUBLICATIONS

"2008 Chinese Milk Scandal," Wikipedia, accessed at https://web.archive.org/web/20140702094551/http://en.wikipedia.org/wiki/2008_Chinese_milk_scandal, last modified on Jun. 11, 2014, pp. 42.

(Continued)

*Primary Examiner* — Abdullahi Nur

(57) ABSTRACT

A method for the quality control of dairy products is disclosed. The method includes scanning the surface of a dairy product test sample using a chromatic scanner system to generate a spectral pattern of reflected light intensities, which pattern is unique to the test sample. The spectral pattern from the test sample is compared with spectral patterns from one or more reference dairy products to provide an indication of test sample identify, quality and/or nutritional content.

27 Claims, 10 Drawing Sheets

(56) References Cited

U.S. PATENT DOCUMENTS

2009/0255473 A1* 10/2009 Katz ............... A23C 19/02
119/14.08
2010/0315644 A1  12/2010 Egan et al.

OTHER PUBLICATIONS

"Beecher's Handmade Cheese," accessed at http://www.beechershandmadecheese.com/, accessed on Jan. 31, 2017, pp. 2.
"How the Dairy Quality Device Works," Dairy Quality inc., accessed at https://web.archive.org/web/20130827155339/http://dairyquality.com/howitworks.php, accessed on Jan. 30, 2017, pp. 2.
International Search Report and Written Opinion for International Application No. PCT/US2014/050393 dated Jan. 14, 2015, pp. 14.
Kalinin, A., et al., "Determining the composition of proteins in milk using a portable near infrared spectrometer," Journal of Near Infrared Spectroscopy, vol. 21, Issue 5, pp. 409-415 (2013).

* cited by examiner

QUALITY CONTROL OF DAIRY PRODUCTS USING CHROMATIC PROFILES

CROSS-REFERENCE TO RELATED APPLICATION

This application is a U.S. National Stage filing under 35 U.S.C. § 371 of International Application No. PCT/US2014/050393, filed on Aug. 8, 2014, the disclosure of which is incorporated by reference in its entirety.

BACKGROUND

Unless otherwise indicated herein, the materials described in this section are not prior art to the claims in this application and are not admitted to be prior art by inclusion in this section.

Dairy products are stock food and the major source of nutrients for human growth and health. Due to the large consumption, the quality control of dairy products has been a concern for many. There are infamous incidents where the breach of dairy product safety causes death, such as the 2008 Chinese milk scandal that resulted in 13 infant deaths and more than 54,000 hospitalized. These incidents involve watered-down milk and infant formula adulterated with melamine. Melamine contamination has been found in other food materials and components. The World Health Organization referred to the incident as one of the largest food safety events it had had to deal with in recent years, and that the crisis of confidence among Chinese consumers would be hard to overcome. A spokesman said the scale of the problem proved it was "clearly not an isolated accident, but a large-scale intentional activity to deceive consumers for simple, basic, short-term profits."

U.S. Pat. No. 5,844,680 is directed to a device and process for measuring and analyzing spectral radiation, in particular for measuring and analyzing color characteristics. In particular, a number of radiation sources are provided in combination with a sensor for detecting radiation within a desired wavelength range. The radiation sources have spectral characteristics that are linearly independent from one another, but overlap so that in combination, the radiation sources generate radiation over the entire desired wavelength range. Alternatively, a single radiation source is provided that generates radiation over the entire desired wavelength range, in combination with a plurality of sensors that have spectral sensing characteristics that are linearly independent from one another, but overlap the entire desired wavelength range. A control unit stores a number of calibration functions with linearly independent spectral characteristics.

SUMMARY

In accordance with one embodiment, a method for quality control of dairy products is disclosed. The method includes: providing a chromatic scanner system, which includes a scanner head having light sources, each configured to emit light of a different interrogation wavelength, and one or more photodetectors, each configured to detect an intensity of reflected light for each of the different interrogation wavelengths, the one or more photodetectors further being configured to generate a signal corresponding to the intensity of reflected light; and a controller operably coupled to the scanner head, and configured to activate the light sources in accordance with a predetermined sequential pattern, receive the corresponding signals from the one or more photodetectors, and generate a spectral pattern of reflected light intensities. A surface of a dairy product test sample is scanned using the scanner head to generate a spectral pattern unique to the test sample. The spectral pattern from the test sample is compared with spectral patterns from one or more reference dairy products.

In accordance with another embodiment, a chromatic scanner system is disclosed for quality control of dairy products. The scanner system includes: a scanner head having light sources, each configured to emit light of a different interrogation wavelength, and one or more photodetectors, each configured to detect an intensity of reflected light for each of the different interrogation wavelengths, the one or more photodetectors further being configured to generate a signal corresponding to the intensity of reflected light; and a controller operably coupled to the scanner head, and configured to activate the light sources in accordance with a predetermined sequential pattern, receive the corresponding signals from the one or more photodetectors, and generate a spectral pattern of reflected light intensities. The controller includes an operable coupling for accessing spectral patterns from a plurality of dairy products stored on a database accessible to the controller through the operable coupling.

A dairy product reference database is disclosed in accordance with another embodiment. The reference database includes a plurality of spectral patterns, each spectral pattern being characteristic of a reference dairy product and includes light intensities reflected at two or more wavelengths from a surface of the reference dairy product.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

Figure 1:
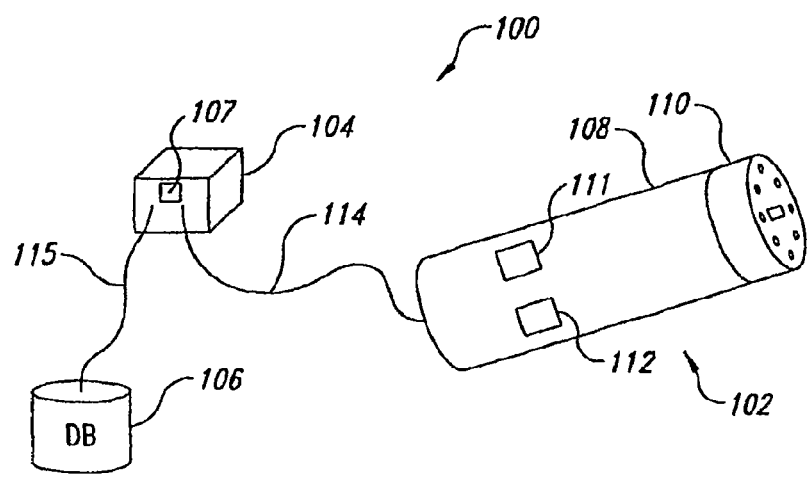
FIG. 1 shows an chromatic scanner system according to one embodiment.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Colorimetric Technologies

The ability to recognize, identify, verify, authenticate and/or classify objects has numerous commercial applications. It may be useful in some applications to determine whether an object being evaluated is identical to a previously evaluated object; in other words determine whether an object being sampled is the exact same object as a reference object. Alternatively, it may be useful to determine whether an object being evaluated is similar to a reference object; in other words determine whether an object being sampled is a facsimile of the reference object.

For example, it may be useful to determine whether a manufactured object is identical to, or has the same spectral characteristics of a previously evaluated manufactured object. Such may be useful in authenticating goods, and deterring counterfeiting or gray marketing of goods. Such may also be useful in manufacturing process control and/or quality control, such as the quality control of dairy products. Also for example, it may also be useful to determine whether other objects, such as paintings or other works of art are identical to a previously sampled work of art.

It may be particular useful where the above may occur based on the natural conditions or attributes of the object, media, or biological tissue, without the need to apply dedicated indicia such as serial numbers, machine-readable symbols (for example, barcode symbols, area or matrix code symbols, stack code symbols), and/or radio frequency identification (RFID tags.) Such dedicated data carriers may, in some embodiments, provide additional information regarding the object.

All of the above may, or may not employ additional information about the object to facilitate the process. Additional information may include one or more measurable or observable physical characteristics of the object, media or biological tissue, for example, height, weight, age, hair or eye color, gender, location, type, size, denomination, serial numbers, security features, name, type, serial numbers, date of issue, color, and so on Such additional information may be employed to confirm a match, or to reduce the number of reference responses for comparison with a test response.

The ability to perform such in a network environment may provide a variety of distinct advantages. For example, such may make possible low cost end user test devices, which share or gain remote access to higher cost computing hardware and software. Such may allow the costs of the computing hardware and software to be shared over a variety of end users or financial entities. Such may also allow for "centralization" of relatively higher cost computing hardware and software, perhaps permitting use of high speed super-computers that could not otherwise be financially justified for individual end users or small groups of end users. Such also may allow for "decentralization" of low cost sampling or test device. Such may also allow for light weight and/or low power consuming test devices. Such may additionally or alternatively permit the upgrade of previously distributed test devices. Such may also permit the distribution of work load. Such may also facilitate the backing up of data, and provide for redundancy. Other advantages will be apparent from the teachings herein.

In certain embodiments, devices, systems and methods for measuring and analyzing the spectral characteristics of colors, that is, of radiation which is in the visible wavelength range of 380 nanometers to 780 nanometesr (nm). The embodiments disclosed herein, however, are not restricted to the range of visible light but may also be used for radiation having a shorter or, as the case may be, longer wavelength. Such devices, systems and methods have been disclosed, for example in U.S. Pat. Nos. 5,844,680 and 8,076,630; the entire disclosures of which are incorporated herein by reference.

The color of surfaces is a fundamental characteristic of all objects, including gases, liquids, solids and combinations thereof, such as colloids, suspensions, emulsions, and so on The sensation created by color occurs, for example, in the case of an illuminated surface where the incident light is absorbed or reflected in such a way that the light reflected from the surface displays a specific spectral course which is perceived by the observer as color. In order to manufacture colors and colored surfaces in a reproducible way it may be desirable to determine the spectral characteristic.

Knowledge of the spectral characteristics of color may also be desirable in order to accurately reproduce color by photographic methods, that is in printed matter or on film, and so on, and in particular, in order to detect color by electronic means, to transfer the recorded data, and to accurately reproduce color on the television screen and the visual display unit.

The spectral distribution of the light which, for example, is reflected from a colored object, and which creates a specific color sensation is referred to as the color stimulus function $\varphi(\lambda)$. On the one hand, the color stimulus function is determined by the spectral distribution of the light $S(\lambda)$ which strikes the object, and on the other hand by the reflectance function $\sigma(\lambda)$ which depends on the wavelength characterizes the reflectivity. The color stimulus function is expressed as follows:

$$\varphi(\lambda)=\sigma(\lambda)\cdot S(\lambda)$$

This means that the color stimulus function is the product of the spectral distribution of the light source, and the reflectance function.

If the light is not reflected from the object but passes through the object, the reflectance function is replaced with the transmission function $\tau(\lambda)$.

As the color stimulus function is a function of the spectral distribution of the light which strikes the surface, this means that the color sensation may change, if the spectral power distribution changes. Such differences can be observed, for example, when an object is first illuminated with natural light metamerism and then with artificial light.

It has been shown that the color sensation which a color elicits from a so-called standard observer can be described in terms of three variables, so-called primary variables. According to this theory the color values, X, Y, and Z, of one color, which are elicited by the color stimulus function $\varphi(\lambda)$ are determined by means of the following integrations:

$X=k\int_\lambda \sigma(\lambda)X(\lambda)d\lambda$
$Y=k\int_\lambda \sigma(\lambda)Y(\lambda)d\lambda$
$Z=k\int_\lambda \sigma(\lambda)Z(\lambda)d\lambda$ X, Y, and Z are the color values, $\sigma(\lambda)$ is the color stimulus function, whereas x, y, and z are the standard spectral value function as a function of $\lambda$. In 1931, a corresponding standard for color values was established by the CIE (Commission Internationale de l'Eclairage) for the observation of small areas of color, in particular, at a visual angle of 2°. As a supplement to this system, a 10° system was introduced in 1964. In addition to these standards, there are also other color standards which have been established by other standards organizations, which, as a rule, are based on the Young-Helmholtz three-color theory.

There are a plurality of devices for measuring the color characteristics of an object, the most important of which are briefly described in the following.

A typical passive colorimeter measures the radiation emitted by an object, as a result of its own radiation or reflection, by means of three photosensitive detectors. A filter is positioned in front of each of the detectors, by means of which the aforementioned spectral value functions $x(\lambda)$, $y(\lambda)$ and $z(\lambda)$ are reproduced. The color values X, Y, and Z can be calculated directly from the values measured by means of the sensors and then displayed. A disadvantage of this device, however, is that the filter functions must be extremely accurate reproductions of the spectral value functions, which is very costly. Moreover, these devices cannot record metameric effects.

The so-called spectrophotometer are another kind of colorimeter. This device is equipped, for example, with 16 or 32 narrow band filters along with a sensor, so that the intensity of the reflected light can be detected in a narrow wavelength range. This makes it possible to determine the reflectance function as a function of the wavelength over the respective wavelength ranges, from which the spectral distribution of this function can be plotted. During this process, however, a separate filter is required for each point on the spectral distribution curve which is used as a value. This also has the disadvantage that the construction of the device and particularly the manufacturing of the narrow band filter is very costly, which means that these devices are generally used in the laboratory only.

In the case of another type of spectrophotometer the reflected light is split either by means of a prism, in which case the refraction is a function of the wavelength, or a grid, in which case the diffraction is also a function of the wavelength. These instruments, however, are very costly as regards their construction so that they too are used primarily in the laboratory.

The monochromator is another known colorimeter which permits the light of a specific wavelength only to strike the sample, which in turn makes it possible to detect the spectral distribution exactly. This device, however, is also very costly and like the spectrophotometer it is used preferably in the laboratory.

There have already been numerous endeavors to develop colorimeter which would be suitable for use outside the laboratory, that is, in the manufacturing of goods and the like.

In one colorimeter, such as that described in DE 42 02 822 A1, the device is equipped with a cylindrical substrate, on one side of which a temperature sensor is mounted and on the other side of which light sources arranged in a circle are mounted and separated from a group of four photosensitive sensors by means of a cylindrical wall. The device is equipped further with a plurality of optical fibers, along which light can be guided from the light source to the area to be measured, where the light is reflected and guided to the sensors by way of the optical fibers.

Each of the light sources and sensors have different spectral characteristics. The light sources are supplied in turn with energy and the light reflected in each case is measured by means of the detectors.

A set of weighted integrations is then generated, where the number of integrations is the product of the number of light sources multiplied by the number of detectors. The weighting functions of the integrations are the product of the respective illumination weighting function and the respective sensor weighting function. From this set of weighted integration values, a set of weighted integration values is calculated by means of linear transformation, by the use of predetermined coefficients used for the transformation. It is thus possible to calculate standard color values by using component parts whose spectral characteristics do not correspond to the characteristics for determining standard color values.

Chromatic Scanner System

With reference to FIG. 1, an embodiment of the chromatic scanner system is illustrated. The chromatic scanner system 100 includes an scanner head 102, a computer system 104, and a database 106. The scanner head 102 includes a controller 108 and a transducer unit 110. The controller 108 includes driver electronics 111 and signal processing electronics 112. In certain embodiments, the controller 108 is operably coupled to the scanner head 102, but may be a separate unit. The controller 108 may in some embodiments be physically incorporated in the computer system 104. The coupling between the controller and the scanner head could be any coupling means known in the art, including direct coupling means, such as wires and optical couplers, as well as indirect, signal transmission/reception couplings, such as radiofrequency, IR, and so on The computer system 104 may take any of a variety of forms, for example, personal computers, mini-computers, work stations, or main frame computers, tablets, smart phones, and so on The computer system 104 may, for example, take the form of a server computer executing server software. Computer system 104 is well known in the art, and may include a computing device 107, memory, input/output devices, and peripherals. The computing device 107 may be a microprocessor, a central processing unit (CPU), or a virtual device running on the CPU, for example. The memory may include volatile and nonvolatile memory, such as RAM and ROM, and/or include other forms of mass storage devices, including one or more hard disks or RAID drives, CD/ROMs, or other mass storage devices.

In another embodiment, the controller 108 of the scanner head 102 includes the computer system 104. For example, the controller 108 may include the computing device 107 (for example, a microprocessor) and memory, as well as user-operable switches and/or a keypad with an electronic display.

The memory may store evaluation software executable by the microprocessor for operating the scanner head 102. A user may program the evaluation software to control the scanner head 102. In another embodiment, the scanner head 102 includes the controller 108, the computer 104 and the database 106.

As illustrated in FIG. 1, the scanner head 102 is communicatively coupled to the computer system 104 via a first communication cable 114. The first communication cable 114 enables the computer system 104 to send and receive data, control, and power signals to the object test device 102. Additionally, the computer system 104 is communicatively coupled to the database 106 via a second communication cable 115. In another embodiment, the scanner head 102, the computer system 104 and the database 106, or any combination thereof, may be configured to support wireless communication of data, control and power signals. Additionally, or alternatively, the scanner head 102, computer system 104 and/or database 106 may be communicatively coupled by one or more networks (not shown). The network can take a variety of forms, for example one or more local area networks (LANs), wide area networks (WANs), wireless LANs (WLANs), and/or wireless WANs (WWANs). The network may employ packet switching or any other type of transmission protocol. The network may, for example, take the form of the Internet or Worldwide Web portion of the Internet. The network may take the form of public switched telephone network (PSTN) or any combination of the above, or other networks known in the art.

Figure 2:
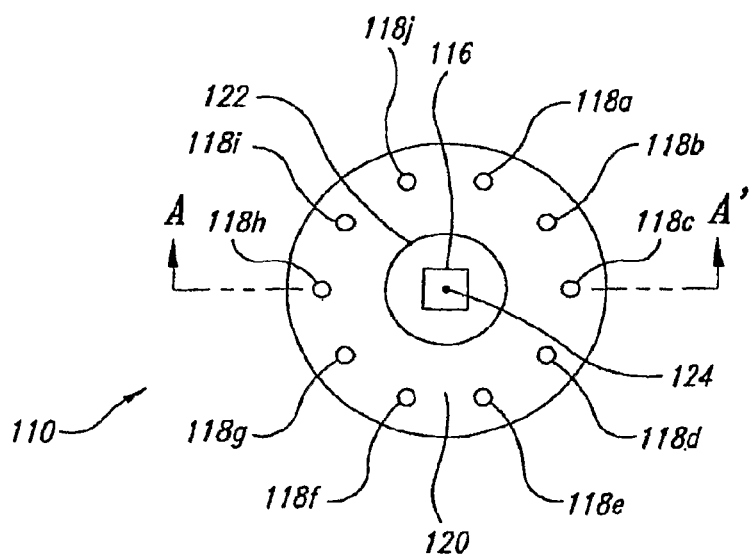
FIG. 2 is an end view showing a transducer unit (scanner head) of the chromatic scanner system illustrated in FIG. 1.

FIG. 2 is an end view of the transducer unit 110 of the scanner head 102 illustrated in FIG. 1. The transducer unit 110 includes a sensor 116 and N radiation sources 118a-118j (collectively 118), where N is a positive integer. The radiation sources 118 may also be referred to herein as light sources, although the type of electromagnetic energy emission (radiation) is not limited to the light spectrum. For ease of illustration, FIG. 2 shows ten radiation sources (that is, N=10), however any number of sources may be employed. The sources 118a-118j emit electromagnetic energy. Each of the sources 118a-118j may emit electromagnetic energy in a respective band of the electromagnetic spectrum. If the sources 118a-118j are driven at the same power level by the driver electronics 111, then in one embodiment, each source has an emission spectrum that is different from the emission spectra of the other sources. In another embodiment, at least one source has an emission spectrum that is different from the emission spectra of the other sources. In one embodiment, the radiation sources 118a-118j are light emitting diodes (LEDs). In yet another embodiment, the radiation sources 118a-118j are tunable lasers. Alternatively, or additionally, the sources 118a-118j may take the form of one or more incandescent sources such as conventional or halogen light bulbs. Alternatively, or additionally, the sources may take the form of one or more organic LEDs (OLEDs, also referred to in the relevant art as "electronic paper"), which may advantageously be formed on a flexible substrate. Alternatively, or additionally, the sources 118a-118j may, for example, take the form of one or more sources of microwave, radio wave or X-ray electromagnetic energy.

One, more or all of the radiation sources 118a-118j may be operable to emit in part or all of an "optical" portion of the electromagnetic spectrum, including the (human) visible portion, near infrared portion and/or or near ultraviolet portions of the electromagnetic spectrum. Additionally, or alternatively, the sources 118a-118j may be operable to emit electromagnetic energy other portions of the electromagnetic spectrum, for example the infrared, ultraviolet and/or microwave portions.

In some embodiments, at least some of the sources 118 are operable to emit in or at a different band than other of the sources 118. For example, one or more sources 118 may emit in a band centered around 450 nm, while one or more of the sources 118 may emit in a band centered around 500 nm, while a further source or sources emit in a band centered around 550 nm. In some embodiments, each source 118 emits in a band centered around a respective frequency or wavelength, different than each of the other sources 118. Using sources 118 with different band centers advantageously maximizes the number of distinct samples that may be captured from a fixed number of sources 118. This may be particularly advantageous where the scanner head 102 is relatively small, and has limited space or footprint for the radiation sources.

Further, the spectral content for each of the sources 118 may vary according to a drive level (for example, current, voltage, duty cycle), temperature, and other environmental factors. Thus, the emission spectra of each of the sources 118 may have at least one of a different center, bandwidth and/or other more complex differences in spectral content, such as those described above (for example, width of the band, the skew of the distribution, the kurtosis, and so on) from those of the other sources 118. Such variation may be advantageously actively employed to operate one or more of the sources 118 as a plurality of "logical sources," each of the logical sources operable to provide a respective emission spectra from a respective source 118. Thus, for example, the center of the band of emission for LEDs may vary according to drive current and/or temperature. One way the spectral content can vary is that the peak wavelength can shift. However, the width of the band, the skew of the distribution, the kurtosis, and so on, can also vary. Such variations may be also be advantageously employed to operate the sources 118 as a plurality of logical sources. Thus, even if the peak wavelength were to remain constant, the changes in bandwidth, skew, kurtosis, and any other change in the spectrum can provide useful variations in the operation of the scanner head 102. Likewise, the center of the band of emission may be varied for tunable lasers. Varying the center of emission bands for one or more sources 118 advantageously maximizes the number of samples that may be captured from a fixed number of sources 118. Again, this may be particularly advantageous where the scanner head 102 is relatively small, and has limited space or footprint for the sources 118.

A field of emission of one or more sources 118 may be movable with respect to a housing. For example, one or more sources 118 may be movable mounted with respect to the housing, such as mounted for translation along one or more axes, and/or mounted for rotation or oscillation about one or more axes. Alternatively, or additionally, the scanner head 102 may include one or more elements operable to deflect or otherwise position the emitted electromagnetic energy. The elements may, for example, include one or more optical elements, for example lens assemblies, mirrors, prisms, diffraction gratings, and so on For example, the optical elements may include an oscillating mirror, rotating polygonal mirror or prism, or MEMS micro-mirror that oscillates about one or more axes. The elements may, for example, include one or more other elements, example permanent magnets or electromagnets such as those associated with cathode ray tubes and/or mass spectrometers. Structures for moving the field of emission and the operation of such are discussed in more detail below.

The sensor 116 can take a variety of forms suitable for sensing or responding to electromagnetic energy. For example, the sensor 116 may take the form of one or more photodetectors, including various photodiodes (for example, germanium photodiodes, silicon photodiodes). Alternatively, or additionally, the sensor 116 may take the form of one or more CMOS image sensors. Alternatively, or additionally, the sensor 116 may take the form of one or more charge couple devices (CCDs). Alternatively, or additionally the sensor 116 may take the form of one or more microchannel plates. Other forms of electromagnetic sensors may be employed, which are suitable to detect the wavelengths expected to be returned in response to the particular illumination and properties of the object being illuminated.

The sensor 116 may be formed as individual elements, one-dimensional array of elements and/or two-dimensional array of elements. For example, the sensor 116 may be formed by one germanium photodiode and one silicon photodiode, each having differing spectral sensitivities. For example, the scanner head 102 may employ a number of photodiodes with identical spectral sensitivities, with different colored filters (for example, gel filters, dichroic filters, thin-film filters, etc) over the photodiodes to change their spectral sensitivity. This may provide a simple, low-cost approach for creating a set of sensors with different spectral sensitivities, particularly since germanium photodiodes are currently significantly more expensive that silicon photodiodes. Alternatively, or additionally, the sensor 116 may take the form of one or more photomultiplier tubes. For example, the sensor 116 may be formed from one CCD array (one-dimensional or two-dimensional) and one or more photodiodes (for example, germanium photodiodes and/or silicon photodiodes). For example, the sensor 116 may be formed as a one- or two-dimensional array of photodiodes. A two-dimensional array of photodiodes enables very fast capture rate (that is, camera speed) and may be particular suited to use is assembly lines or high speed sorting operations. For example, the sensor 116 may be formed as a one- or two-dimensional array of photomultipliers. Combinations of the above elements may also be employed.

In some embodiments, the sensor 116 may be a broadband sensor sensitive or responsive over a broad band of wavelengths of electromagnetic energy. In some embodiments, the sensor 116 may be a narrowband sensor sensitive or responsive over a narrow band of wavelengths of electromagnetic energy. In some embodiments, the sensor 116 may take the form of several sensor elements, as least some of the sensor elements sensitive or responsive to one narrow band of wavelengths, while other sensor elements are sensitive or responsive to a different narrow band of wavelengths. This approach may advantageously increase the number of samples that may be acquired using a fixed number of sources. In such embodiments the narrow bands may, or may not, overlap.

In some embodiments, the radiation or light source 118 may also serve as the sensor 116. For example, an LED may be operated to emit electromagnetic energy at one time, and detect returned electromagnetic energy at another time. For example, the LED may be switched from operating as a source to operating as a detector by reverse biasing the LED. Also for example, an LED may be operated to emit electromagnetic energy at one time, and detect returned electromagnetic energy at the same time, for example by forward biasing the LED.

A field of view of the sensor 116 or one or more elements of the sensor 116 may be movable with respect to the housing. For example, one or more elements of the sensor 116 may be movably mounted with respect to the housing, such as mounted for translation along one or more axes, and/or mounted for rotation or oscillation about one or more axes. Alternatively, or additionally, the scanner head 102 may include one or more elements operable to deflect or otherwise position the returned electromagnetic energy. The elements may, for example, include one or more optical elements, for example lens assemblies, mirrors, prisms, diffraction gratings, and so on For example, the optical elements may include an oscillating mirror, rotating polygonal mirror or prism, or MEMS micro-mirror that oscillates about one or more axes. The elements may, for example, include one or more other elements, example permanent magnets or electromagnets such as those associated with cathode ray tubes and/or mass spectrometers.

In some embodiments, the source 118 may also serve as the sensor 116. For example, an LED may be operated to emit electromagnetic energy at one time, and detect returned electromagnetic energy at another time. Also for example, an LED may be operated to emit electromagnetic energy at one time, and detect returned electromagnetic energy at the same time.

The radiation sources 118a-118j are mounted on a source end plate 120 and the sensor 116 is mounted on a sensor end plate 122. In another embodiment, the source and sensor end plates 120 and 122, respectively, form a single contiguous plate. As illustrated, the sources 118a-118j are mounted on the source end plate 120 to form a circle, with the sensor 116 mounted along an axis 124 that is normal to the source end plate 120 and which passes approximately through a center of the circle. The sensor 116 may be located at any position along the axis 124, as will be discussed further below with reference to FIG. 3.

In operation, a user may instruct the computer system 104 via software to drive the sources 118a-118j in a selected sequence with an electromagnetic forcing function. A source emits electromagnetic energy when driven by the electromagnetic forcing function. In one embodiment, the computer system 104 drives the sources 118a-118j via the driver electronics 111. The driver electronics 111 may include any combination of switches, transistors and multiplexers, as known by one of skill in the art or later developed, to drive the sources 118a-118j in a selected drive pattern. As mentioned above, the computer system functions may be subsumed within the controller functions or the controller functions may be subsumed within the computer system.

The electromagnetic forcing function may be a current, a voltage and/or duty cycle. In one embodiment, a forcing function is a variable current that drives one or more of the sources 118a-118j in the selected drive pattern (also referred to as a selected sequence). In one embodiment, the computer system 104 drives the sources 118a-118j (or any subset of the sources 118a-118j) in the selected sequence, in which only one or zero sources are being driven at any given instant of time. In another embodiment, the computer system 104 drives two or more sources at the same time for an overlapping time period during the selected sequence. The computer system 104 may operate automatically, or may be responsive to input from a user. Use of the electromagnetic forcing function to drive the sources as a number of logical sources is also envisioned.

Figure 3:
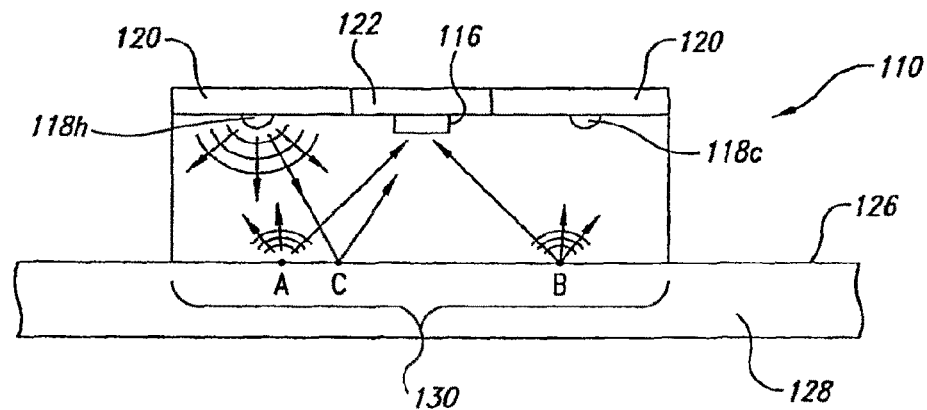
FIG. 3 is a cross-sectional diagram showing an A-A' cross-section of the transducer unit illustrated in FIG. 2.

With reference to FIG. 3, the transducer unit 110 is illustrated. The transducer unit 110 may be placed proximate a surface 126 of an evaluation object 128 that is the subject of evaluation. The evaluation object 128 includes objects that reflect, refract, transmit, fluoresce, phosphoresce and/or absorb and re-radiate or otherwise return incident electromagnetic energy. The evaluation object 128 may be in any state of matter, including solid, liquid or gaseous states. Each of the sources 118a-118j, when driven, illuminates a portion 130 of the surface 126 of the evaluation object 128. As used herein, the terms illuminate, interrogate, illuminates, illumination, and variations of such terms mean to expose to or reveal by the use of electromagnetic energy or electromagnetic radiation, whether in the visible portion of the electromagnetic spectrum, the optical portion (for example, visible, near-infrared, near-ultraviolet), or other portions (for example, far-infrared, far-ultraviolet, microwave, X-ray, and so on).

Typically, the evaluation object 128 reflects, emits, fluoresces or otherwise returns an electromagnetic response to the illumination. The spectral content of the electromagnetic response depends upon the spectrum of the electromagnetic energy incident upon the evaluation object 128 and upon the physical, chemical and electrical properties of the evaluation object 128. Some or all of the electromagnetic response is incident upon the sensor 116.

For example, as illustrated in FIG. 3, driver electronics 111 drives source 118*h* via a user-adjustable electromagnetic forcing function to emit electromagnetic energy. The electromagnetic energy emitted by source 118*h* illuminates a portion 130 of the surface 126 of the evaluation object 128. Based in part upon the contour of the surface 126 and the electrical and chemical properties of the object 128, an electromagnetic response from some or all of the illuminated portion 130 of the surface 126 is received by the sensor 116. For example, an electromagnetic response received by the sensor 116 may be composed of electromagnetic energy emitted from points A and B of the surface 126, comprising reflected and/or re-radiated or otherwise returned light. Other points on the surface 126 may only return electromagnetic energy incident from the source 118*h*. For example, point C only returns electromagnetic energy incident from the source 118*h*. The returned electromagnetic energy from points A, B and C is incident upon the sensor 116. For illustrative ease, only three points A, B and C on the surface 126 are shown to contribute to the electromagnetic response, but many other portions of the surface 126 may also contribute to the response.

Figure 4A:
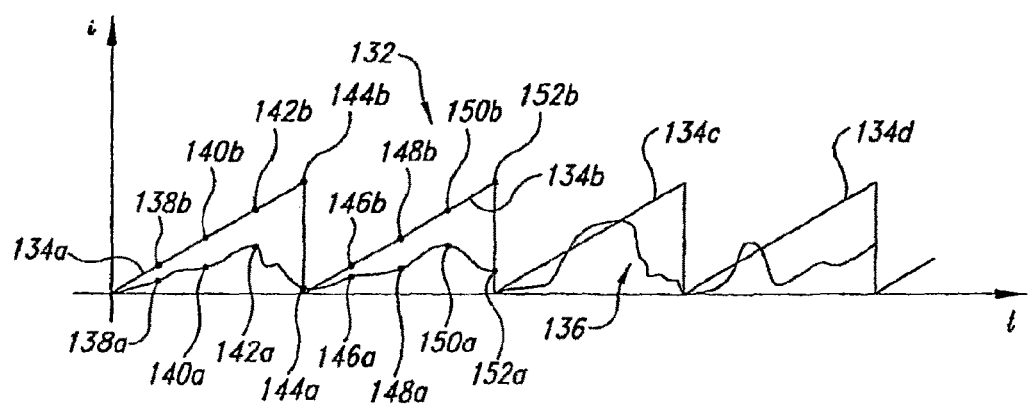
FIG. 4A-4C are graphs illustrating a portion of an exemplary electromagnetic forcing function that drives light sources of the scanner head as a plurality of logical sources.
Figure 4B:
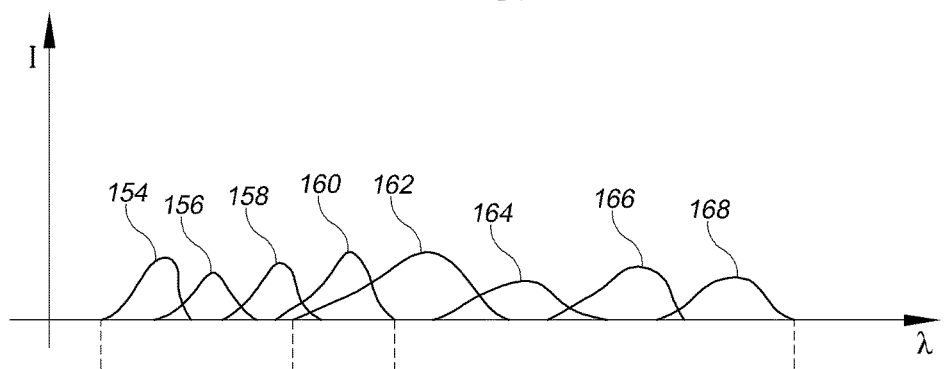
Figure 4C:
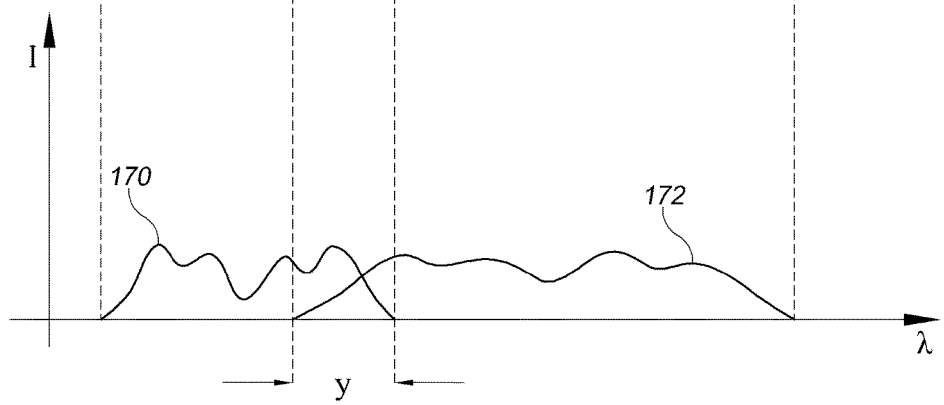

FIGS. 4A-4C illustrate a portion of an electromagnetic forcing function 132 that drives the sources 118*a*-118*j* as a plurality of logical sources, according to one illustrated embodiment.

In this embodiment, the electromagnetic forcing function 132 is a time varying current with a saw-tooth pattern. The electromagnetic forcing function 132 comprises a plurality of segments 134*a*-134*d* (collectively 134). For ease of illustration, FIG. 4A illustrates four segments 134*a*-134*d*, however, any suitable number of segments may be employed. In operation, each segment 134 of the electromagnetic forcing function 132 drives one source of the sources 118*a*-118*j* as a number of logical sources. According to one embodiment, the number of logical sources is greater than the number of sources 118*a*-118*j*. Logical sources will be discussed further below with reference to FIG. 4B.

As an exemplary embodiment, segment 134*a* drives source 118*a*, segment 134*b* drives source 118*b*, segment 134*c* drives source 118*c* and segment 134*d* drives source 118*d*. A user may instruct the computer system 104 to drive any number of the sources 118*a*-118*j* in a selected sequence. A user may program the selected sequence via the evaluation software, where the evaluation software may be stored in the memory of the computer system 104. The microprocessor executes the evaluation software programmed by the user and controls the driver electronics 111 in driving the sources 118*a*-118*j* by the electromagnetic forcing function 132 in the selected sequence.

For example, a user or computer system 104 may select to drive the sources 118*a*-118*j* in a spatially uniform sequence in which the sources 118*a*-118*j* are driven in an order in which they are mounted on the source end plate 120 (for example, {118*a*, 118*b*, 118*c*, ..., 118*i*, 118*j*}), or in a spatially non-uniform sequence, such as (118*a*, 118*d*, 118*j*, 118*i*, 118*e*, 118*c*, 118*b*, 118*g*, 118*h*, 118*f*). Typically, the selected sequence is repeated until the user or computer system 104 selects a different sequence or the object test device 102 is powered OFF. In another embodiment, the user or computer system 104 may select a subset of the sources 118*a*-118*j* to be driven in a selected sequence.

As discussed above, the sequence defines an order of activation for the sources 118, and may optionally define a sequence of drive levels for respective ones of the sources 118 within the sequence. In some embodiments, the sequence can be varied periodically. In other embodiments, the sequence may be varied randomly. In further embodiments, the sequence may be varied with each iteration. In still other embodiments, the sequence may be varied based on a time and/or date. Varying the sequence produces an inherent encryption of the signals indicative of the test responses and/or the results. The variation makes it difficult for someone to determine or fake test responses for a given object since the test response varies based on the particular illumination sequence employed. This may be particularly advantageous were security is a concern, for example where identity documents are being authenticated, where financial instruments are being authenticated or where goods are being authenticated to detect forgeries. Thus, the sequence may be varied randomly, periodically, based on time and/or date, or on demand. This inherent variation may be bolstered by more conventional encryption, for example public/private key encryption, for example RSA encryption. Thus, the test response may be encrypted using conventional encryption techniques. Additionally, or alternatively, the sequence may be encrypted using conventional encryption techniques. Additionally, or alternatively, if the sequence is transmitted, it may be transmitted separately from the test results, reducing the likelihood of interception of both. It should be noted that even if both the sequence and resulting test response were intercepted, such information would have limited value since the sequence would or could soon be changed.

Additionally, FIG. 4A illustrates a response signal 136 generated by the sensor 116 upon receiving an electromagnetic response emitted by the evaluation object 128 in response to illumination by the sources 118*a*-118*j* (or a subset of the sources) being driven in the selected sequence by the electromagnetic forcing function 132. In one embodiment, the test response signal 136 is an electrical signal 136. As illustrated, the signal processing electronics 112 (FIG. 1) samples the test response signal 136 at a predetermined sampling rate, as indicated by sampling points 138*a*, 140*a*, 142*a*, ..., 152*a*.

According to one embodiment, the electromagnetic forcing function 132 drives each source 118 as a plurality of logical sources. That is, a source 118 may be considered to be composed of a plurality of logical sources, where each logical source of a given source has a respective emission spectrum based upon a value of the electromagnetic forcing function 132 driving the given source 118 and upon optical characteristics of the given source 118. For example, since the test response signal 136 is sampled four times as a given source 118 is being driven, the given source 118 operates as four logical sources, where each logical source has a respective emission spectrum or band, different from the emission spectrum or band of the other logical sources for that particular source 118. That is, the number of logical sources depends upon the electromagnetic forcing function 132 and the sampling rate of the test response signal 136.

FIG. 4B illustrates four emission spectra 154, 156, 158 and 160 of four logical sources corresponding to the source 118*a* being driven by the forcing function 132 at points 138*b*, 140*b*, 142*b*, and 144*b*, and four emission spectra 162, 164, 166 and 168 of four logical sources corresponding to the physical source 118*b* being driven by the forcing function 132 at points 146*b*, 148*b*, 150*b*, and 152*b*. As illustrated, some emission spectra of the emission spectra 154-168 of the logical sources overlap, however, in an alternate embodiment none of the emission spectra 154-168 overlap with any other of the emission spectra 154-168.

FIG. 4C illustrates a composite emission spectrum 170 for source 118a and a composite emission spectrum 172 for source 118b. The composite emission spectrum for any given source is a summation of the emission spectra of the logical sources for the given source. Thus, composite emission spectrum 170 is a summation of the emission spectra 154, 156, 158 and 160 corresponding to the four logical sources generated by driving the source 118a at points 138b, 140b, 142b and 146b of the forcing function 132, and composite emission spectrum 172 is a summation of the emission spectra 162, 164, 166 and 168 corresponding to the four logical sources generated by driving the source 118b at points 146b, 148b, 150b and 152b of the forcing function 132. As illustrated, the composite emission spectra of the sources 118a and 118b overlap one another in a region Y. However, any combination of overlapping and non-overlapping composite emission spectra corresponding to the selected sequence of physical sources being driven may be employed.

Figure 5:
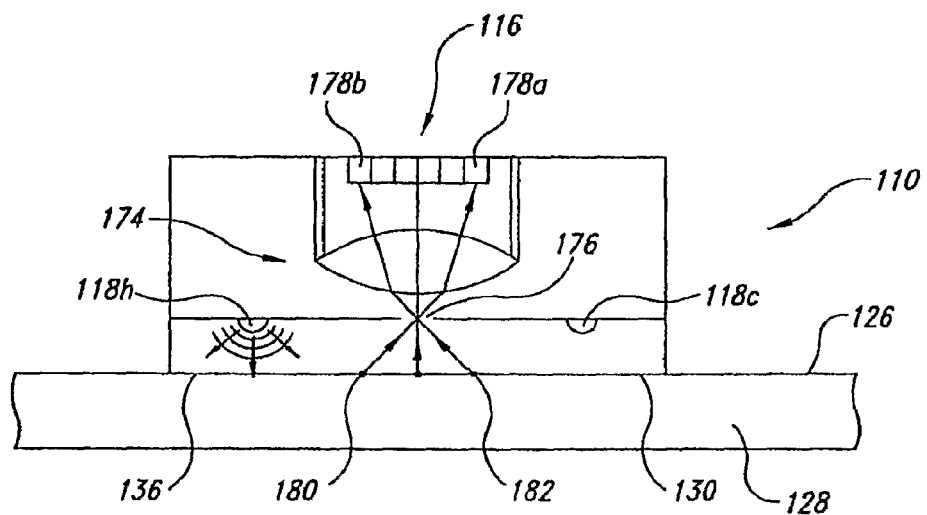
FIG. 5 is a cross-sectional diagram showing an A-A' cross-section of the transducer unit illustrated in FIG. 2.

FIG. 5 shows the transducer unit 110 according to another illustrated embodiment. The transducer unit 110 includes a focusing device 174 and an aperture 176. However, in other embodiments, the transducer unit 110 may include only the focusing device 174 or only the aperture 176. In this embodiment, the sensor 116 is a detector array having detectors 178. In operation, each source driven in a selected sequence emits electromagnetic energy toward the portion 130 of the surface 126 of the evaluation object 128. Each detector receives an electromagnetic response returned from a respective portion of the illuminated portion 130 of the evaluation object 128. For example, when source 118h is driven, the focusing device 174 focuses an electromagnetic response returned from a respective region 180 of the illuminated portion 130 onto a detector 178a and an electromagnetic response from a respective region 182 of the illuminated portion 130 onto a detector 178b. When source 118c is driven, the focusing device 174 focuses a different electromagnetic response from the respective region 180 of the illuminated portion 130 onto the detector 178a.

Each detector (collectively 178) converts an electromagnetic response characteristic of a respective region of the illuminated portion 130 of the evaluation object 128 into a signal characteristic of the respective region. If the sensor 116 includes M detectors 178, then M signals are produced. The signals may be stored in the database 106 (FIG. 1) for further analysis. The focusing device 174 and the aperture 176 allow for a highly reliable evaluation of the evaluation object 128 against known reference objects, since each detector generates a signal that is indicative of an electromagnetic response for a respective sub-portion (that is, region) of the portion 130. In contrast, the signal generated by the sensor 116 (FIG. 3) is indicative of an electromagnetic response for the portion 130. That is, the signal generated by the sensor 116 is a weighted average of the signals generated by the detectors 178.

Figure 6:
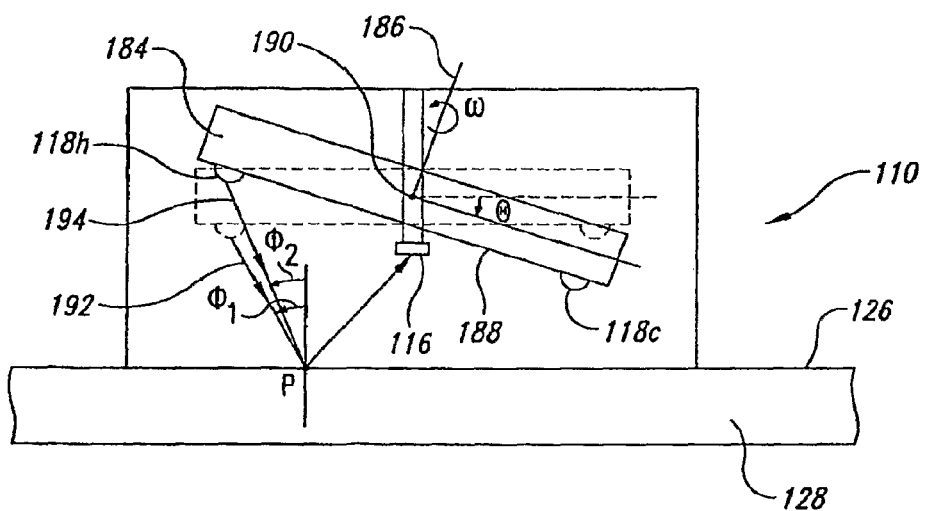
FIG. 6 is a cross-sectional diagram showing an A-A' cross-section of the transducer unit illustrated in FIG. 2.

FIG. 6 shows the transducer unit 110 according to still another illustrated embodiment. The transducer unit 110 includes a source mount assembly 184 to which the sources 118a-118j are mounted. In one embodiment, the source mount assembly 184 is moveable with respect to the evaluation object 128. In another embodiment, the source mount assembly 184 is moveable with respect to the evaluation object 128 and the sensor 116.

As illustrated in FIG. 6, the source mount assembly 184 is rotatable at a user-defined angular velocity ω about an axis 186, where the axis 186 is perpendicular to a surface 188 of the source mount assembly 184 to which the light sources are mounted. The source mount assembly 184 may also be pivotable by a user-defined elevation angle θ about an axis 190, where the axis 190 is perpendicular to the axis 186.

When any given source emits electromagnetic energy, an angle of incidence of the electromagnetic energy at a given point on the surface 126 of the evaluation object 128 depends upon the elevation angle θ. As illustrated, when the elevation angle θ is zero, φ1 is the angle of incidence of electromagnetic energy (represented by a ray 192) at a point P on the surface 126. However, when the elevation angle θ is greater than zero, then φ2 is the angle of incidence of electromagnetic energy (represented by a ray 194) at the point P on the surface 126. Thus, an electromagnetic response may be obtained by driving the sources in a selected sequence for a number of different elevation angles θ to illuminate the evaluation object 128.

In an exemplary embodiment, the evaluation object 128 is illuminated by driving the sources 118 in the selected sequence for a first elevation angle (for example, θ=0°), driving the sources in the selected sequence for a second elevation angle (for example, θ=10°), and then driving the sources in the selected sequence for a third elevation angle (for example, θ=20°). The illuminated object 128 emits an electromagnetic response, a portion of which is detected by the sensor 116. The sensor 116 produces a signal indicative of the electromagnetic response. For a given sampling rate, the signal contains three times more data as compared to a signal obtained by driving the sources in the selected sequence at only the first elevation angle.

In one further aspect, the current level to the LEDs can be varied, thereby shifting its peak wavelength. This allows flexibility in design of such scanners and coverage of essentially any interrogation wavelength. The small shifts in the peak wavelength achievable by varying current level, effectively allows the scanner to get multiple wavelengths from a single LED source. The changes in the reaction of the material under test to these small shifts in wavelength can be a part of the ChromaID pattern' thereby enhancing the ability of the technology to distinguish test materials and make positive identifications. Examples of this technique of varying current level can be found in U.S. Pat. No. 7,996,173; the entire disclosure of which is incorporated herein by reference.

Numerous other variations in a chromatic scanner system have been described. See for example, U.S. Pat. No. 8,076,630; also incorporated in its entirety by reference.

EXAMPLES

Additional embodiments are disclosed in further detail in the following examples, which are not in any way intended to limit the scope of the claims.

A commercial chromatic scanner (CHROMAID™; Visualant, Inc.; Seattle, Wash., USA) was used to generate quality control data for a variety of different dairy products having different fat and protein contents. The scan head used for the experiments disclosed herein contains 12 light emitting diodes (LEDs) to emit radiation of across a broad spectrum of wavelengths, including UV, visible and near IR wavelengths. Light was emitted in accordance with a predetermined sequential pattern to interrogate the surface of the dairy product being tested. The chromatic scanner included 4 photodiode detectors for monitoring the intensity of light reflected off the surface of the dairy product for each of LED irradiation wavelengths. In some embodiments, a low-cost device may comprise a minimum number of LEDs and detector (for example, as few as one of each). In some embodiments, the LED light source could also serve the function of a detector.

Example 1

Chromatic Profiles for Milk Product Samples having Different Fat Contents

Four different milk samples were scanned using the commercial ChromaID scanner system in accordance with the manufacturer's instructions. The scanner head was placed normal to the surface of the milk samples in open containers at 1 cm distance from the surface of the milk. The samples included Sample A is Heritage Farm Skim Milk, Grade A; Sample B is Heritage Farm 1% Reduced Fat Milk, Grade A; Sample C is Heritage Farm 2% Reduced Fat Milk, Grade A; and Sample D is Heritage Farm Whole Milk, Grade A. Nutritional information about the test milk samples are as follows:

|  | A | B | C | D |
|---|---|---|---|---|
| TOTAL FAT | 0 | 2.5 | 5 | 8 |
| SATURATED FAT | 0 | 1.5 | 3 | 5 |

The chromatic profiles are shown in the following series of tables, where the wavelengths of the 12 LED light sources (EMT01-EMT12) go from 355 nm up to 1450 nm. The 4 photodiodes (DET01, DET02, DET03, DET04) detected reflected light in the 1) Visible, 2) UV, 3) IR, and 4) Visible wavelengths respectively. Separate data tables are provided for each of the photodetectors (DET 01-DET 04). The LEDs were run at between 1 and 100% levels (in these example, at approximately 0, 11, 22, 33, 44, 56, 67, 78, 89, and 100% of maximum output intensity). The columns show there were 10 firings (interrogations) of each LED (top row). The first block of numbers is readings on a first visible photodiode detector (DET01), the second block is for the UV detector (DET02), the third block is for the IR detector (DET03), and the fourth block is for another visible detector (DET04). DET01 had a response range of 380 nm-1100 nm, DET02 had a response range of 290 nm-370 nm, DET03 had a response range of 900 nm-1700 nm, and DET04 had a response range 380 nm-1100 nm. These range indications are truncated in the respective displayed tables.

The ChromaID inspection of the milk products revealed differences in the relative light intensity at the wavelength of 810 nm, 910 nm, and 970 nm that correspond to the LED EMT06 (810 nm), 10 (910 nm), 12 (970 nm). The intensities of the reflected light varied between milk samples, but seems to correlate with the fat content in the milk, especially at LED EMT10 (910 nm). The intensity trends up significantly when the LEDs were run at 80-100 % intensity. This data demonstrates that scanning the surface of milk to generate a chromatic profile can be used to evaluate the fat content of the milk. A comparison of the intensity of reflected light over control (skim milk) increased by 1% for 1% milk and 8% for whole milk.

| | | 0.000000% | 11.111111% | 22.222222% | 33.333333% | 44.444444% | 55.555556% | 66.666667% | 77.777778% | 88.888889% | 100.00000% |
|---|---|---|---|---|---|---|---|---|---|---|---|
| DET01 | 380 nm-1100 nm | Level | Level | Level | Level | Level | Level | Level | Level | Level | Level |
| Visible | | | | | | | | | | | |
| EMT01 | 355 nm | 0.390631 | 0.422162 | 0.466734 | 0.507969 | 0.542867 | 0.573695 | 0.596029 | 0.616217 | 0.630629 | 0.642413 |
| EMT02 | 395 nm | 0.412482 | 1.130128 | 2.090681 | 3.09422 | 4.087025 | 5.078549 | 6.062311 | 7.037938 | 7.98474 | 8.922983 |
| EMT03 | 468 nm | 0.427699 | 0.907314 | 1.248348 | 1.531279 | 1.778759 | 2.003884 | 2.222175 | 2.426183 | 2.619797 | 2.802491 |
| EMT04 | 574 nm | 0.392336 | 0.445223 | 0.50748 | 0.570011 | 0.622636 | 0.675196 | 0.723377 | 0.767601 | 0.805056 | 0.84185 |
| EMT05 | 595 nm | 0.407362 | 0.455344 | 0.517064 | 0.591266 | 0.656283 | 0.731599 | 0.817144 | 0.888693 | 0.958431 | 1.029164 |
| EMT08 | 630 nm | 0.399745 | 0.645888 | 0.934464 | 1.232559 | 1.552791 | 1.883567 | 2.20024 | 2.514768 | 2.829266 | 3.129876 |
| EMT11 | 700 nm | 0.389284 | 0.946695 | 1.626116 | 2.366221 | 3.142417 | 3.92769 | 4.722431 | 5.527205 | 6.342686 | 7.153142 |
| EMT06 | 810 nm | 0.432134 | 4.686356 | 9.02179 | 13.33229 | 17.61738 | 21.86241 | 26.09321 | 30.26157 | 34.37973 | 38.45475 |
| EMT10 | 910 nm | 0.40983 | 6.734628 | 16.41264 | 27.11459 | 38.24755 | 49.60532 | 61.0362 | 72.4929 | 83.90546 | 95.2487 |
| EMT12 | 970 nm | 0.420851 | 1.502949 | 2.7084 | 3.894115 | 5.061853 | 6.181491 | 7.284994 | 8.340491 | 9.406573 | 10.43232 |
| EMT09 | 1200 nm | 0.461769 | 0.461769 | 0.50664 | 0.556147 | 0.591844 | 0.632685 | 0.664342 | 0.691879 | 0.717157 | 0.750214 |
| DET02 | 1450 nm | 0.4201 | 0.422746 | 0.423151 | 0.413173 | 0.40279 | 0.398392 | 0.39801 | 0.387895 | 0.392348 | 0.40555 |
| | 290 nm-370 nm | 0.000000% | 11.111111% | 22.222222% | 33.333333% | 44.444444% | 55.555556% | 66.666667% | 77.777778% | 88.888889% | 100.00000% |
| UV | | Level | Level | Level | Level | Level | Level | Level | Level | Level | Level |
| EMT01 | 355 nm | 0.043327 | 0.028199 | 0.0458 | 0.044554 | 0 | 0 | 0.031734 | 0.013083 | 0.041556 | 0.037599 |
| EMT02 | 395 nm | 0.010651 | 0.00602 | 0.027806 | 0.071782 | 0.00906 | 0 | 0.007635 | 0.003052 | 0 | 0.017172 |
| EMT03 | 468 nm | 0.014675 | 0.008225 | 0.008947 | 0.017363 | 0.005519 | 0.002229 | 0.028539 | 0 | 0.010723 | 0.019693 |
| EMT04 | 574 nm | 0.029838 | 0.012118 | 0.011414 | 0.007141 | 0 | 0.007153 | 0.02681 | 0 | 0 | 0.02225 |
| EMT05 | 595 nm | 0.00928 | 0.017458 | 0.006282 | 0.009406 | 0 | 0 | 0.031 | 0.011486 | 0 | 0 |
| EMT08 | 630 nm | 0 | 0 | 0.003344 | 0.032866 | 0.02507 | 0.014132 | 0 | 0.000286 | 0 | 0 |
| EMT11 | 700 nm | 0 | 0.029653 | 0.013882 | 0 | 0.009668 | 0.003576 | 0 | 0.012636 | 0 | 0 |
| EMT06 | 810 nm | 0.008142 | 0 | 0.019562 | 0.009823 | 0 | 0.005895 | 0.010383 | 0.029159 | 0.052923 | 0.013697 |
| EMT10 | 910 nm | 0.022215 | 0.028402 | 0 | 0 | 0.030792 | 0.028223 | 0.026691 | 0.011939 | 0.008172 | 0.004208 |
| EMT12 | 970 nm | 0.01722 | 0.026107 | 0 | 0.024533 | 0 | 0 | 0.016624 | 0.023842 | 0.011045 | 0.022888 |
| EMT09 | 1200 nm | 0 | 0.002295 | 0.025994 | 0 | 0.026435 | 0.002247 | 0 | 0.009644 | 0.00152 | 0 |
| EMT07 | 1450 nm | 0.00568 | 0.003135 | 0 | 0 | 0 | 0 | 0 | 0 | 0 | 0 |
| DET03 | 900 nm-1700 nm | 0.000000% | 11.111111% | 22.222222% | 33.333333% | 44.444444% | 55.555556% | 66.666667% | 77.777778% | 88.888889% | 100.00000% |
| IR | | Level | Level | Level | Level | Level | Level | Level | Level | Level | Level |
| EMT01 | 355 nm | 0.069481 | 0.064552 | 0.067234 | 0.06851 | 0.063956 | 0.071532 | 0.073451 | 0.066221 | 0.066203 | 0.076848 |
| EMT02 | 395 nm | 0.066972 | 0.068116 | 0.072104 | 0.068033 | 0.073212 | 0.082242 | 0.08232 | 0.079727 | 0.084823 | 0.090766 |
| EMT03 | 468 nm | 0.06966 | 0.068361 | 0.077349 | 0.071239 | 0.056112 | 0.07419 | 0.076157 | 0.075012 | 0.078583 | 0.082445 |
| EMT04 | 574 nm | 0.065851 | 0.067139 | 0.074893 | 0.068057 | 0.065595 | 0.07025 | 0.068349 | 0.06808 | 0.073737 | 0.072336 |
| EMT05 | 595 nm | 0.06451 | 0.06628 | 0.072426 | 0.070602 | 0.069588 | 0.073093 | 0.06634 | 0.070977 | 0.074095 | 0.073934 |
| EMT08 | 630 nm | 0.06578 | 0.073081 | 0.077915 | 0.080317 | 0.09169 | 0.093317 | 0.098848 | 0.104952 | 0.110513 | 0.110739 |
| EMT11 | 700 nm | 0.068933 | 0.063485 | 0.074691 | 0.082093 | 0.086933 | 0.084233 | 0.092596 | 0.098121 | 0.10401 | 0.113601 |
| EMT06 | 810 nm | 0.066102 | 0.294495 | 0.534558 | 0.759298 | 0.991756 | 1.221736 | 1.443523 | 1.67163 | 1.900977 | 2.120018 |
| EMT10 | 910 nm | 0.065297 | 0.149262 | 0.268382 | 0.410908 | 0.558114 | 0.693578 | 0.83437 | 0.987285 | 1.135594 | 1.27812 |
| EMT12 | 970 nm | 0.079525 | 0.102109 | 0.14385 | 0.199938 | 0.237322 | 0.276172 | 0.316006 | 0.355017 | 0.384802 | 0.425756 |
| EMT07 | 1200 nm | 0.066233 | 0.879031 | 1.517874 | 2.078015 | 2.583832 | 3.04997 | 3.473699 | 3.871626 | 4.242987 | 4.602504 |
| EMT09 | 1450 nm | 0.065738 | 0.216985 | 0.335366 | 0.442189 | 0.53944 | 0.620157 | 0.695878 | 0.771093 | 0.83341 | 0.891984 |
| DET04 | 380 nm-1100 nm | 0.000000% | 11.111111% | 22.222222% | 33.333333% | 44.444444% | 55.555556% | 66.666667% | 77.777778% | 88.888889% | 100.00000% |
| Visible | | Level | Level | Level | Level | Level | Level | Level | Level | Level | Level |
| EMT01 | 355 nm | 0.414181 | 0.439537 | 0.452811 | 0.476593 | 0.481749 | 0.51316 | 0.518745 | 0.548184 | 0.578761 | 0.586814 |
| EMT02 | 395 nm | 0.414932 | 1.283819 | 2.440518 | 3.63164 | 4.829222 | 6.003851 | 7.168472 | 8.308769 | 9.44152 | 10.54089 |
| EMT03 | 468 nm | 0.386471 | 1.176995 | 1.743835 | 2.213419 | 2.632773 | 3.018749 | 3.37447 | 3.714902 | 4.036284 | 4.343868 |
| EMT04 | 574 nm | 0.41377 | 0.508678 | 0.615501 | 0.738472 | 0.848258 | 0.961924 | 1.074743 | 1.189095 | 1.294494 | 1.385695 |
| EMT05 | 595 nm | 0.424373 | 0.517511 | 0.629413 | 0.741315 | 0.863928 | 0.974017 | 1.085705 | 1.188535 | 1.298475 | 1.392233 |
| EMT08 | 630 nm | 0.42702 | 0.608587 | 0.830692 | 1.059461 | 1.290047 | 1.504231 | 1.752335 | 1.976001 | 2.206481 | 2.430368 |

-continued

| | | 0.423545 | 0.718641 | 1.080299 | 1.469678 | 1.877046 | 2.285379 | 2.716053 | 3.133709 | 3.567368 | 4.020787 |
|---|---|---|---|---|---|---|---|---|---|---|---|
| EMT11 | 700 nm | 0.390971 | 7.852048 | 15.39533 | 22.92124 | 30.39762 | 3.780344 | 45.14506 | 52.42109 | 59.60147 | 66.68137 |
| EMT06 | 810 nm | 0.402677 | 1.792056 | 3.917051 | 6.280912 | 8.741529 | 11.2623 | 13.79081 | 16.31344 | 18.82925 | 21.32589 |
| EMT10 | 910 nm | 0.407648 | 1.122362 | 1.918191 | 2.711058 | 3.471691 | 4.19752 | 4.915059 | 5.610317 | 6.281478 | 6.938762 |
| EMT12 | 970 nm | 0.407237 | 0.450426 | 0.478894 | 0.515515 | 0.537002 | 0.576401 | 0.621378 | 0.660074 | 0.690407 | 0.721073 |
| EMT07 | 1200 nm | 0.403947 | 0.408089 | 0.415814 | 0.423539 | 0.422442 | 0.424993 | 0.420666 | 0.418693 | 0.409275 | 0.409263 |
| EMT09 | 1450 nm | | | | | 1% Milk | | | | | |
| DET01 | 380 nm– | 0.000000% | 11.11111% | 22.22222% | 33.33333% | 44.44444% | 55.55556% | 66.66667% | 77.77778% | 88.88889% | 100.00000% |
| Visible | 1100 nm | Level | Level | Level | Level | Level | Level | Level | Level | Level | Level |
| EMT01 | 355 nm | 0.574094 | 0.609046 | 0.635839 | 0.666261 | 0.68351 | 0.705057 | 0.706106 | 0.736052 | 0.741357 | 0.744605 |
| EMT02 | 395 nm | 0.525367 | 1.257116 | 2.227271 | 3.219668 | 4.219461 | 5.199665 | 6.162549 | 7.105244 | 8.036572 | 8.942569 |
| EMT03 | 468 nm | 0.55238 | 1.024878 | 1.35594 | 1.629073 | 1.877558 | 2.116794 | 2.35312 | 2.57448 | 2.7771 | 2.975971 |
| EMT04 | 574 nm | 0.575316 | 0.620723 | 0.670588 | 0.720155 | 0.764775 | 0.810748 | 0.849944 | 0.892901 | 0.930816 | 0.968593 |
| EMT05 | 595 nm | 0.539291 | 0.603128 | 0.693351 | 0.7756 | 0.854439 | 0.927878 | 1.000929 | 1.067555 | 1.129133 | 1.189607 |
| EMT08 | 630 nm | 0.547423 | 0.817347 | 1.144934 | 1.477391 | 1.808214 | 2.14219 | 2.467096 | 2.789557 | 3.106529 | 3.416407 |
| EMT11 | 700 nm | 0.554323 | 1.164836 | 1.910269 | 2.709574 | 3.525859 | 4.357988 | 5.211139 | 6.069297 | 6.934095 | 7.803149 |
| EMT06 | 810 nm | 0.54841 | 5.787945 | 11.09058 | 16.393 | 21.67863 | 26.93653 | 32.15026 | 37.31326 | 42.39684 | 47.42502 |
| EMT10 | 910 nm | 0.569892 | 7.400722 | 17.88015 | 29.45787 | 41.51602 | 53.81593 | 66.20561 | 78.60177 | 90.9676 | 99.19501 |
| EMT12 | 970 nm | 0.531185 | 1.848579 | 3.326363 | 4.798001 | 6.236226 | 7.626099 | 8.985395 | 10.29452 | 11.56984 | 12.80918 |
| EMT07 | 1200 nm | 0.572246 | 0.632 | 0.683814 | 0.721175 | 0.765801 | 0.805539 | 0.840014 | 0.875717 | 0.904381 | 0.954503 |
| EMT09 | 1450 nm | 0.540662 | 0.527924 | 0.526917 | 0.522983 | 0.543684 | 0.552434 | 0.566399 | 0.568605 | 0.573975 | 0.574625 |
| DET02 | 290 nm– | 0.000000% | 11.11111% | 22.22222% | 33.33333% | 44.44444% | 55.55556% | 66.66667% | 77.77778% | 88.88889% | 100.00000% |
| UV | 370 nm | Level | Level | Level | Level | Level | Level | Level | Level | Level | Level |
| EMT01 | 355 nm | 0.00903 | 0.055712 | 0.009298 | 0.012738 | 0.006425 | 0.02405 | 0.021523 | 0.026202 | 0.041145 | 0.023448 |
| EMT02 | 395 nm | 0.019485 | 0 | 0.013584 | 0.021058 | 0.000942 | 0.017953 | 0.001788 | 0.002795 | 0.004297 | 0.019699 |
| EMT03 | 468 nm | 0 | 0.018054 | 0.035411 | 0 | 0 | 0.015247 | 0.008476 | 0 | 0 | 0 |
| EMT04 | 574 nm | 0.012541 | 0.018972 | 0.054073 | 0.054073 | 0.021297 | 0.001365 | 0.066507 | 0.003088 | 0.004196 | 0 |
| EMT05 | 595 nm | 0 | 0.009632 | 0.002283 | 0.021529 | 0 | 0.009388 | 0.006229 | 0.035959 | 0.004363 | 0 |
| EMT08 | 630 nm | 0.016546 | 0.005698 | 0 | 0.03022 | 0 | 0.006998 | 0.012672 | 0.010848 | 0.015712 | 0.005829 |
| EMT11 | 700 nm | 0.003982 | 0.027162 | 0.014383 | 0.015706 | 0.022167 | 0 | 0 | 0 | 0.050408 | 0 |
| EMT06 | 810 nm | 0.015867 | 0.000483 | 0.000685 | 0.009078 | 0.022167 | 0.025374 | 0.044137 | 0 | 0.031453 | 0.027251 |
| EMT10 | 910 nm | 0.016445 | 0 | 0.011736 | 0.011736 | 0.001097 | 0.011116 | 0.010967 | 0.017077 | 0.000411 | 0.025612 |
| EMT12 | 970 nm | 0.019765 | 0 | 0.015479 | 0.028449 | 0.042802 | 0 | 0.02408 | 0.012887 | 0.000548 | 0.006855 |
| EMT07 | 1200 nm | 0.006312 | 0.005782 | 0.003988 | 0.007641 | 0.015354 | 0.00459 | 0 | 0 | 0 | 0 |
| EMT09 | 1450 nm | 0.025827 | | | | | | | | | |
| DET03 | 900 nm– | 0.000000% | 11.11111% | 22.22222% | 33.33333% | 44.44444% | 55.55556% | 66.66667% | 77.77778% | 88.88889% | 100.00000% |
| IR | 1700 nm | Level | Level | Level | Level | Level | Level | Level | Level | Level | Level |
| EMT01 | 355 nm | 0.071847 | 0.072145 | 0.072277 | 0.066769 | 0.071162 | 0.066406 | 0.072348 | 0.069892 | 0.067532 | 0.069404 |
| EMT02 | 395 nm | 0.074458 | 0.059134 | 0.076449 | 0.080425 | 0.07391 | 0.08201 | 0.083828 | 0.084382 | 0.087225 | 0.089026 |
| EMT03 | 468 nm | 0.076187 | 0.072104 | 0.076604 | 0.080556 | 0.07931 | 0.074863 | 0.080109 | 0.076693 | 0.082999 | 0.086445 |
| EMT04 | 574 nm | 0.06755 | 0.072765 | 0.070089 | 0.074637 | 0.071776 | 0.065452 | 0.068492 | 0.074494 | 0.075108 | 0.077963 |
| EMT05 | 595 nm | 0.069088 | 0.073594 | 0.072891 | 0.078018 | 0.074118 | 0.071365 | 0.072902 | 0.070554 | 0.077182 | 0.076175 |
| EMT08 | 630 nm | 0.069815 | 0.074852 | 0.081718 | 0.083691 | 0.096011 | 0.090092 | 0.10916 | 0.10554 | 0.11974 | 0.111538 |
| EMT11 | 700 nm | 0.074339 | 0.072342 | 0.081444 | 0.080103 | 0.093383 | 0.091732 | 0.103122 | 0.10727 | 0.115591 | 0.120497 |
| EMT06 | 810 nm | 0.073016 | 0.302398 | 0.546652 | 0.783211 | 1.020587 | 1.253605 | 1.493144 | 1.721096 | 1.952267 | 2.190292 |
| EMT10 | 910 nm | 0.064689 | 0.175113 | 0.322276 | 0.503224 | 0.674838 | 0.860548 | 1.044029 | 1.232851 | 1.409024 | 1.582903 |
| EMT12 | 970 nm | 0.064607 | 0.127375 | 0.189394 | 0.266153 | 0.325 | 0.386453 | 0.444287 | 0.503069 | 0.549877 | 0.611627 |
| EMT07 | 1200 nm | 0.068307 | 0.898433 | 1.544243 | 2.111173 | 2.619183 | 3.092873 | 3.529877 | 3.941495 | 4.316599 | 4.684288 |
| EMT09 | 1450 nm | 0.079095 | 0.222558 | 0.346762 | 0.45315 | 0.549054 | 0.634033 | 0.711173 | 0.784373 | 0.84917 | 0.920713 |
| DET04 | 380 nm– | 0.000000% | 11.11111% | 22.22222% | 33.33333% | 44.44444% | 55.55556% | 66.66667% | 77.77778% | 88.88889% | 100.00000% |
| Visible | 1100 nm | Level | Level | Level | Level | Level | Level | Level | Level | Level | Level |
| EMT01 | 355 nm | 0.512469 | 0.546992 | 0.58291 | 0.624025 | 0.652891 | 0.684094 | 0.703436 | 0.720877 | 0.733364 | 0.740838 |

| | | | | | | | | | |
|---|---|---|---|---|---|---|---|---|---|
| EMT02 | 395 nm | 0.552779 | 1.387864 | 2.522731 | 3.682918 | 4.856015 | 6.007398 | 7.170267 | 8.316851 | 9.434826 | 10.54225 |
| EMT03 | 468 nm | 0.572562 | 1.358438 | 1.910031 | 2.371979 | 2.776987 | 3.150708 | 3.498489 | 3.839511 | 4.148579 | 4.455495 |
| EMT04 | 574 nm | 0.513667 | 0.631994 | 0.752044 | 0.878984 | 0.998443 | 1.111537 | 1.215816 | 1.305956 | 1.393563 | 1.472426 |
| EMT05 | 595 nm | 0.545669 | 0.625658 | 0.740975 | 0.832993 | 0.963932 | 1.081097 | 1.215816 | 1.338124 | 1.457954 | 1.566976 |
| EMT08 | 630 nm | 0.538236 | 0.729042 | 0.97726 | 1.221663 | 1.485008 | 1.756656 | 2.02328 | 2.293086 | 2.552605 | 2.810908 |
| EMT11 | 700 nm | 0.534272 | 0.863916 | 1.288116 | 1.727224 | 2.220136 | 2.713543 | 3.199059 | 3.714013 | 4.217691 | 4.71499 |
| EMT06 | 810 nm | 0.565618 | 8.973707 | 17.47593 | 25.98295 | 34.42093 | 42.83824 | 51.16023 | 59.40487 | 67.53572 | 75.57884 |
| EMT10 | 910 nm | 0.523144 | 2.440065 | 5.359018 | 8.577604 | 11.93079 | 15.32898 | 18.76583 | 22.17295 | 25.57241 | 28.94277 |
| EMT12 | 970 nm | 0.539064 | 1.503194 | 2.543801 | 3.589756 | 4.592681 | 5.565483 | 6.508011 | 7.438297 | 8.342255 | 9.240163 |
| EMT07 | 1200 nm | 0.560617 | 0.6001 | 0.659812 | 0.715792 | 0.763977 | 0.802118 | 0.847787 | 0.877512 | 0.911796 | 0.93528 |
| EMT09 | 1450 nm | 0.521427 | 0.566775 | 0.556576 | 0.556546 | 0.541264 | 0.540137 | 0.526881 | 0.521821 | 0.511551 | 0.521451 |

2% Milk

| | | | | | | | | | |
|---|---|---|---|---|---|---|---|---|---|
| DET01 Visible | 380 nm–1100 nm | 0.000000% Level | 11.11111% Level | 22.222222% Level | 33.333333% Level | 44.444444% Level | 55.555556% Level | 66.666667% Level | 77.777778% Level | 88.888889% Level | 100.000000% Level |
| EMT01 | 355 nm | 0.492495 | 0.519663 | 0.546444 | 0.591266 | 0.633174 | 0.663859 | 0.694615 | 0.722408 | 0.742817 | 0.753045 |
| EMT02 | 395 nm | 0.526303 | 1.255518 | 2.24399 | 3.258699 | 4.281944 | 5.284667 | 6.280494 | 7.259715 | 8.247811 | 9.213329 |
| EMT03 | 468 nm | 0.522542 | 1.023281 | 1.376552 | 1.668722 | 1.930338 | 2.166218 | 2.380938 | 2.592921 | 2.78551 | 2.980417 |
| EMT04 | 574 nm | 0.487918 | 0.532031 | 0.596637 | 0.669348 | 0.737155 | 0.799763 | 0.855851 | 0.906408 | 0.954384 | 0.993645 |
| EMT05 | 595 nm | 0.523144 | 0.57509 | 0.649488 | 0.714213 | 0.793934 | 0.858867 | 0.934166 | 1.023048 | 1.105881 | 1.187533 |
| EMT08 | 630 nm | 0.517553 | 0.78032 | 1.119913 | 1.445288 | 1.796746 | 2.136469 | 2.50082 | 2.866644 | 3.21883 | 3.5689 |
| EMT11 | 700 nm | 0.510198 | 1.120877 | 1.888806 | 2.696216 | 3.549856 | 4.420889 | 5.326319 | 6.234193 | 7.144184 | 8.060444 |
| EMT06 | 810 nm | 0.529516 | 6.347418 | 12.24023 | 18.11828 | 23.96993 | 29.77898 | 35.5375 | 41.2363 | 46.8523 | 52.40953 |
| EMT10 | 910 nm | 0.478137 | 7.591344 | 18.48703 | 30.51869 | 43.04634 | 55.806 | 68.68615 | 81.56368 | 94.40361 | 99.09051 |
| EMT12 | 970 nm | 0.532258 | 2.025205 | 3.681124 | 5.318833 | 6.915582 | 8.463497 | 9.973253 | 11.44501 | 12.86563 | 14.26233 |
| EMT07 | 1200 nm | 0.478929 | 0.562066 | 0.64373 | 0.711256 | 0.777829 | 0.830168 | 0.889802 | 0.933015 | 0.96274 | 1.015866 |
| EMT09 | 1450 nm | 0.527275 | 0.532281 | 0.530994 | 0.529492 | 0.52312 | 0.513738 | 0.503701 | 0.502914 | 0.49023 | 0.491267 |
| DET02 UV | 290 nm–370 nm | 0.000000% Level | 11.11111% Level | 22.222222% Level | 33.333333% Level | 44.444444% Level | 55.555556% Level | 66.666667% Level | 77.777778% Level | 88.888889% Level | 100.000000% Level |
| EMT01 | 355 nm | 0.035721 | 0.004804 | 0 | 0.033969 | 0 | 0.026011 | 0.013822 | 0.01772 | 0.035554 | 0.09563 |
| EMT02 | 395 nm | 0.037229 | 0.001842 | 0.009215 | 0 | 0 | 0.009519 | 0 | 0.012165 | 0.014532 | 0.001115 |
| EMT03 | 468 nm | 0.020248 | 0.006634 | 0 | 0.004292 | 0 | 0.01682 | 0 | 0.014764 | 0.002396 | 0 |
| EMT04 | 574 nm | 0.022238 | 0.011903 | 0.026077 | 0 | 0 | 0.016874 | 0 | 0.0112 | 0 | 0 |
| EMT05 | 595 nm | 0.03143 | 0 | 0.033259 | 0.015604 | 0.008631 | 0 | 0.012046 | 0.011367 | 0 | 0 |
| EMT08 | 630 nm | 0.02929 | 0.011986 | 0.030279 | 0.023568 | 0.00186 | 0.010657 | 0.010431 | 0 | 0 | 0 |
| EMT11 | 700 nm | 0.006038 | 0 | 0.019598 | 0 | 0.02175 | 0 | 0 | 0.041091 | 0.004303 | 0.000995 |
| EMT06 | 810 nm | 0.024486 | 0 | 0.019944 | 0.019777 | 0 | 0 | 0.008404 | 0.008404 | 0 | 0 |
| EMT10 | 910 nm | 0.003475 | 0 | 0.040495 | 0.012439 | 0.022244 | 0.007039 | 0.020784 | 0.022084 | 0 | 0 |
| EMT12 | 970 nm | 0.007242 | 0.00326 | 0.015658 | 0.018585 | 0.03249 | 0.050426 | 0.050712 | 0.055522 | 0.017178 | 0.004375 |
| EMT07 | 1200 nm | 0.033963 | 0 | 0.022709 | 0.017607 | 0 | 0.004983 | 0 | 0.02085 | 0 | 0.046152 |
| EMT09 | 1450 nm | 0.008553 | 0.004154 | 0 | 0 | 0 | 0.001538 | 0 | 0 | 0 | 0 |
| DET03 IR | 900 nm–1700 nm | 0.000000% Level | 11.11111% Level | 22.222222% Level | 33.333333% Level | 44.444444% Level | 55.555556% Level | 66.666667% Level | 77.777778% Level | 88.888889% Level | 100.000000% Level |
| EMT01 | 355 nm | 0.070286 | 0.072277 | 0.073117 | 0.078124 | 0.074011 | 0.071061 | 0.076282 | 0.070649 | 0.076371 | 0.070482 |
| EMT02 | 395 nm | 0.068009 | 0.074154 | 0.075036 | 0.083816 | 0.086272 | 0.084591 | 0.089341 | 0.088024 | 0.094616 | 0.095129 |
| EMT03 | 468 nm | 0.051892 | 0.072074 | 0.072604 | 0.082809 | 0.077349 | 0.080681 | 0.077999 | 0.079775 | 0.08716 | 0.089532 |
| EMT04 | 574 nm | 0.075787 | 0.072587 | 0.073087 | 0.076759 | 0.074315 | 0.075382 | 0.076282 | 0.070506 | 0.08319 | 0.076044 |
| EMT05 | 595 nm | 0.076658 | 0.072867 | 0.070447 | 0.080824 | 0.073779 | 0.077564 | 0.078201 | 0.077707 | 0.081301 | 0.08136 |
| EMT08 | 630 nm | 0.074732 | 0.073993 | 0.088245 | 0.092107 | 0.095648 | 0.105292 | 0.106221 | 0.113803 | 0.123602 | 0.123429 |
| EMT11 | 700 nm | 0.076544 | 0.080365 | 0.084591 | 0.101179 | 0.097543 | 0.103611 | 0.090778 | 0.116473 | 0.118607 | 0.123948 |
| EMT06 | 810 nm | 0.0772 | 0.320947 | 0.56327 | 0.821459 | 1.060069 | 1.315194 | 1.560396 | 1.807052 | 2.052337 | 2.291 |
| EMT10 | 910 nm | 0.075156 | 0.184876 | 0.364125 | 0.555092 | 0.746059 | 0.951928 | 1.158077 | 1.365596 | 1.574439 | 1.770955 |
| EMT12 | 970 nm | 0.075525 | 0.146395 | 0.22431 | 0.310576 | 0.386393 | 0.457937 | 0.523639 | 0.592321 | 0.666457 | 0.731307 |

| | | | | | | | | | | |
|---|---|---|---|---|---|---|---|---|---|---|
| EMT07 | 1200 nm | 0.078899 | 0.914222 | 1.579845 | 2.160627 | 2.679724 | 3.152257 | 3.616071 | 4.028505 | 4.430157 | 4.797364 |
| EMT09 | 1450 nm | 0.074828 | 0.231129 | 0.354868 | 0.47735 | 0.561976 | 0.653654 | 0.740653 | 0.813758 | 0.88377 | 0.94344 |
| DET04 | 380 nm– | 0.000000% | 11.111111% | 22.222222% | 33.333333% | 44.444444% | 55.555556% | 66.666667% | 77.777778% | 88.888889% | 100.00000% |
| Visible | 1100 nm | Level | Level | Level | Level | Level | Level | Level | Level | Level | Level |
| EMT01 | 355 nm | 0.511283 | 0.53066 | 0.555581 | 0.569439 | 0.59278 | 0.599098 | 0.614357 | 0.615144 | 0.638735 | 0.663829 |
| EMT02 | 395 nm | 0.493771 | 1.375681 | 2.55661 | 3.770537 | 4.989052 | 6.187124 | 7.371766 | 8.527435 | 9.667749 | 10.79649 |
| EMT03 | 468 nm | 0.473762 | 1.272637 | 1.816446 | 2.294034 | 2.728927 | 3.118164 | 3.489578 | 3.833622 | 4.159487 | 4.475403 |
| EMT04 | 574 nm | 0.511104 | 0.602835 | 0.710052 | 0.809872 | 0.928068 | 1.020748 | 1.125163 | 1.211709 | 1.324898 | 1.422483 |
| EMT05 | 595 nm | 0.504464 | 0.605726 | 0.722632 | 0.847375 | 0.967813 | 1.084411 | 1.197595 | 1.303327 | 1.407588 | 1.504886 |
| EMT08 | 630 nm | 0.506103 | 0.731373 | 0.987816 | 1.264006 | 1.532692 | 1.80552 | 2.071929 | 2.340567 | 2.595383 | 2.860868 |
| EMT11 | 700 nm | 0.511414 | 0.887793 | 1.338124 | 1.821339 | 2.323503 | 2.834469 | 3.351975 | 3.881914 | 4.405874 | 4.943866 |
| EMT06 | 810 nm | 0.472295 | 9.484274 | 18.61145 | 27.75036 | 36.83789 | 45.85856 | 54.79687 | 63.62987 | 72.34893 | 80.93944 |
| EMT10 | 910 nm | 0.499445 | 2.669895 | 6.000913 | 9.687436 | 13.52511 | 17.43414 | 21.39365 | 25.34851 | 29.30181 | 33.20968 |
| EMT12 | 970 nm | 0.463337 | 1.59086 | 2.825237 | 4.054225 | 5.239809 | 6.377704 | 7.499934 | 8.578766 | 9.632731 | 10.64678 |
| EMT07 | 1200 nm | 0.505704 | 0.5715667 | 0.625289 | 0.664955 | 0.718957 | 0.752515 | 0.808787 | 0.850594 | 0.908947 | 0.96271 |
| EMT09 | 1450 nm | 0.467479 | 0.473881 | 0.481433 | 0.495297 | 0.505376 | 0.506198 | 0.515419 | 0.510126 | 0.509256 | 0.504428 |

Whole Milk

| | | | | | | | | | | |
|---|---|---|---|---|---|---|---|---|---|---|
| DET01 | 380 nm– | 0.000000% | 11.111111% | 22.222222% | 33.333333% | 44.444444% | 55.555556% | 66.666667% | 77.777778% | 88.888889% | 100.00000% |
| Visible | 1100 nm | Level | Level | Level | Level | Level | Level | Level | Level | Level | Level |
| EMT01 | 355 nm | 0.46376 | 0.488353 | 0.52579 | 0.572115 | 0.605202 | 0.630587 | 0.65757 | 0.680697 | 0.696993 | 0.705153 |
| EMT02 | 395 nm | 0.494945 | 1.154703 | 2.048809 | 2.966756 | 3.89421 | 4.798061 | 5.719692 | 6.626922 | 7.519454 | 8.390809 |
| EMT03 | 468 nm | 0.502229 | 0.95346 | 1.267511 | 1.534933 | 1.759356 | 1.977205 | 2.154273 | 2.35973 | 2.532643 | 2.71017 |
| EMT04 | 574 nm | 0.464714 | 0.51192 | 0.577551 | 0.635326 | 0.694853 | 0.746191 | 0.799763 | 0.826657 | 0.880748 | 0.909495 |
| EMT05 | 595 nm | 0.482374 | 0.529641 | 0.593197 | 0.655282 | 0.724679 | 0.801313 | 0.882083 | 0.957292 | 1.025468 | 1.095259 |
| EMT08 | 630 nm | 0.473756 | 0.711554 | 1.015407 | 1.319409 | 1.643992 | 1.970053 | 2.305931 | 2.627772 | 2.950287 | 3.26736 |
| EMT11 | 700 nm | 0.471234 | 1.04475 | 1.776749 | 2.556247 | 3.372467 | 4.212773 | 5.057908 | 5.916697 | 6.772268 | 7.635397 |
| EMT06 | 810 nm | 0.493721 | 5.933321 | 11.43029 | 16.92184 | 22.38642 | 27.8095 | 33.18962 | 38.52432 | 43.78859 | 48.98836 |
| EMT10 | 910 nm | 0.473958 | 7.558096 | 18.42122 | 30.4074 | 42.87281 | 55.54781 | 68.32219 | 81.11543 | 93.8824 | 99.21052 |
| EMT12 | 970 nm | 0.49668 | 1.965344 | 3.613854 | 5.232746 | 6.810034 | 8.344025 | 9.844632 | 11.30619 | 12.72894 | 14.12624 |
| EMT07 | 1200 nm | 0.456238 | 0.546345 | 0.617945 | 0.688005 | 0.745267 | 0.798285 | 0.849998 | 0.893271 | 0.933504 | 0.970149 |
| EMT09 | 1450 nm | 0.493801 | 0.492823 | 0.488079 | 0.488913 | 0.476676 | 0.475907 | 0.462568 | 0.464875 | 0.459015 | 0.463438 |
| DET02 | 290 nm– | 0.000000% | 11.111111% | 22.222222% | 33.333333% | 44.444444% | 55.555556% | 66.666667% | 77.777778% | 88.888889% | 100.00000% |
| UV | 370 nm | Level | Level | Level | Level | Level | Level | Level | Level | Level | Level |
| EMT01 | 355 nm | 0.030541 | 0.020456 | 0 | 0.023848 | 0.007284 | 0.032789 | 0.004697 | 0.028366 | 0.026858 | 0.013322 |
| EMT02 | 395 nm | 0.007778 | 0.038731 | 0.027168 | 0 | 0.015104 | 0 | 0.010037 | 0.003713 | 0 | 0.022709 |
| EMT03 | 468 nm | 0.042546 | 0.00664 | 0.000834 | 0.037509 | 0 | 0.017846 | 0 | 0 | 0.011849 | 0.010675 |
| EMT04 | 574 nm | 0.001162 | 0.026107 | 0.026643 | 0.019985 | 0.029147 | 0.026947 | 0 | 0 | 0 | 0.051922 |
| EMT05 | 595 nm | 0.028616 | 0.02715 | 0.022888 | 0.024915 | 0.013292 | 0.013924 | 0.006533 | 0.022936 | 0.003934 | 0.009239 |
| EMT08 | 630 nm | 0 | 0.002337 | 0 | 0.017339 | 0.038511 | 0.031924 | 0 | 0 | 0 | 0 |
| EMT11 | 700 nm | 0.024599 | 0.006211 | 0.033051 | 0.004095 | 0.003093 | 0 | 0 | 0 | 0.0175 | 0.014436 |
| EMT06 | 810 nm | 0.020981 | 0 | 0.037205 | 0.007695 | 0.024194 | 0.012219 | 0.012076 | 0.012654 | 0.011361 | 0.014019 |
| EMT10 | 910 nm | 0.026691 | 0 | 0 | 0.010693 | 0.011432 | 0.013649 | 0.009376 | 0.037283 | 0.036049 | 0.036526 |
| EMT12 | 970 nm | 0 | 0 | 0 | 0.017196 | 0.036567 | 0.019497 | 0 | 0 | 0 | 0 |
| EMT07 | 1200 nm | 0 | 0 | 0 | 0.013125 | 0 | 0 | 0 | 0 | 0 | 0 |
| EMT09 | 1450 nm | 0.003898 | 0.019783 | 0.022155 | 0.033355 | 0 | 0 | 0.003779 | 0.003713 | 0 | 0.036526 |
| DET03 | 900 nm– | 0.000000% | 11.111111% | 22.222222% | 33.333333% | 44.444444% | 55.555556% | 66.666667% | 77.777778% | 88.888889% | 100.00000% |
| IR | 1700 nm | Level | Level | Level | Level | Level | Level | Level | Level | Level | Level |
| EMT01 | 355 nm | 0.075799 | 0.081962 | 0.076479 | 0.078571 | 0.080025 | 0.074947 | 0.080746 | 0.073856 | 0.082564 | 0.077176 |
| EMT02 | 395 nm | 0.078285 | 0.074762 | 0.080508 | 0.085664 | 0.085413 | 0.092065 | 0.086367 | 0.095159 | 0.092167 | 0.089663 |
| EMT03 | 468 nm | 0.076485 | 0.078511 | 0.080353 | 0.082171 | 0.090683 | 0.082111 | 0.085157 | 0.084758 | 0.095445 | 0.083352 |
| EMT04 | 574 nm | 0.075316 | 0.069809 | 0.077617 | 0.081176 | 0.077331 | 0.079644 | 0.080127 | 0.08018 | 0.080329 | 0.093955 |
| EMT05 | 595 nm | 0.085288 | 0.080818 | 0.081223 | 0.078619 | 0.08145 | 0.08145 | 0.088143 | 0.085044 | 0.088173 | 0.086838 |

-continued

| | | | | | | | | | |
|---|---|---|---|---|---|---|---|---|---|
| EMT08 | 630 nm | 0.079268 | 0.081426 | 0.088096 | 0.097632 | 0.097317 | 0.105548 | 0.107497 | 0.120431 | 0.118524 | 0.12815 |
| EMT11 | 700 nm | 0.074792 | 0.080025 | 0.090289 | 0.10289 | 0.102115 | 0.101203 | 0.113875 | 0.11366 | 0.116676 | 0.126243 |
| EMT06 | 810 nm | 0.07835 | 0.313455 | 0.548077 | 0.787216 | 1.014459 | 1.262015 | 1.494551 | 1.733887 | 1.961738 | 2.196008 |
| EMT10 | 910 nm | 0.077462 | 0.186074 | 0.354755 | 0.552511 | 0.736821 | 0.938499 | 1.128495 | 1.32665 | 1.525855 | 1.723379 |
| EMT12 | 970 nm | 0.074077 | 0.149983 | 0.226408 | 0.323218 | 0.397003 | 0.47341 | 0.537258 | 0.619477 | 0.672972 | 0.749987 |
| EMT07 | 1200 nm | 0.080234 | 0.910038 | 1.579052 | 2.123851 | 2.651632 | 3.13313 | 3.581715 | 3.985113 | 4.378403 | 4.745871 |
| EMT09 | 1450 nm | 0.075299 | 0.238341 | 0.372738 | 0.481528 | 0.586867 | 0.668436 | 0.746471 | 0.83099 | 0.90788 | 0.969899 |
| DET04 | 380 nm- | 0.000000% | 11.111111% | 22.222222% | 33.333333% | 44.444444% | 55.555556% | 66.666667% | 77.777778% | 88.888889% | 100.000000% |
| Visible | 1100 nm | Level | Level | Level | Level | Level | Level | Level | Level | Level | Level |
| EMT01 | 355 nm | 0.443876 | 0.458062 | 0.481296 | 0.499338 | 0.514591 | 0.519764 | 0.540209 | 0.550592 | 0.582761 | 0.600779 |
| EMT02 | 395 nm | 0.440937 | 1.238912 | 2.296287 | 3.395772 | 4.490281 | 5.576581 | 6.643147 | 7.695109 | 8.721728 | 9.748692 |
| EMT03 | 468 nm | 0.41492 | 1.142657 | 1.6644 | 2.103126 | 2.493453 | 2.848631 | 3.175903 | 3.504134 | 3.788323 | 4.084212 |
| EMT04 | 574 nm | 0.438774 | 0.52312 | 0.622535 | 0.721884 | 0.824767 | 0.920248 | 1.016891 | 1.115531 | 1.216042 | 1.296491 |
| EMT05 | 595.nm | 0.441104 | 0.527138 | 0.635207 | 0.746149 | 0.853664 | 0.956738 | 1.05508 | 1.160985 | 1.248282 | 1.352906 |
| EMT08 | 630 nm | 0.438625 | 0.641888 | 0.868517 | 1.12828 | 1.371747 | 1.620835 | 1.865739 | 2.115792 | 2.354342 | 2.596009 |
| EMT11 | 700 nm | 0.443143 | 0.786263 | 1.210117 | 1.664031 | 2.116835 | 2.606988 | 3.086132 | 3.585196 | 4.072428 | 4.580057 |
| EMT06 | 810 nm | 0.393289 | 8.861966 | 17.4121 | 25.96787 | 34.46852 | 42.91535 | 51.29698 | 59.58114 | 67.77058 | 75.83949 |
| EMT10 | 910 nm | 0.428236 | 2.542043 | 5.798239 | 9.386916 | 13.12996 | 16.95274 | 20.80055 | 24.64856 | 28.49012 | 32.29847 |
| EMT12 | 970 nm | 0.415558 | 1.528317 | 2.762771 | 3.986836 | 5.177999 | 6.304038 | 7.441199 | 8.524174 | 9.580077 | 10.59716 |
| EMT07 | 1200 nm | 0.426853 | 0.486147 | 0.550026 | 0.592661 | 0.644708 | 0.688154 | 0.746721 | 0.799996 | 0.850177 | 0.900424 |
| EMT09 | 1450 nm | 0.408369 | 0.419235 | 0.428176 | 0.427496 | 0.439012 | 0.440359 | 0.444835 | 0.442863 | 0.436217 | 0.432801 |

Example 2

Chromatic Profiles for Cheese Products of Different Ages

Two different cheese samples were scanned using the commercial ChromaID scanner. The cheeses were Beecher's FLAGSHIP cheese aged 15 months and Beecher's FLAGSHIP cheese aged 4 years. The ChromaID data on the two cheese samples show some significant variations as compared to that of the milk samples. The main difference involves the intensity data as well as the changes of intensity at 355 nm (with EMT01) and 700 nm (with EMT11) vs that at 910 nm (with EMT10) and 970 nm (with EMT12).

| | | Cheese Aged 15 Months | | | | | | | | | |
|---|---|---|---|---|---|---|---|---|---|---|---|
| | | 0.000000% | 11.111111% | 22.222222% | 33.333333% | 44.444444% | 55.555556% | 66.666667% | 77.777778% | 88.888889% | 100.00000% |
| DET01 | 380 nm–1100 nm | Level | Level | Level | Level | Level | Level | Level | Level | Level | Level |
| Visible | | | | | | | | | | | |
| EMT01 | 355 nm | 0.059956 | 0.095999 | 0.140494 | 0.17978 | 0.214702 | 0.245875 | 0.275648 | 0.295043 | 0.325388 | 0.337422 |
| EMT02 | 395 nm | 0.065547 | 0.893974 | 2.022481 | 3.185338 | 4.356593 | 5.510945 | 6.652564 | 7.777316 | 8.874632 | 9.964848 |
| EMT03 | 468 nm | 0.061607 | 0.59008 | 0.956553 | 1.271892 | 1.545411 | 1.806051 | 2.045298 | 2.275276 | 2.494312 | 2.69903 |
| EMT04 | 574 nm | 0.060385 | 0.103724 | 0.153923 | 0.196463 | 0.248408 | 0.297833 | 0.340396 | 0.377959 | 0.427729 | 0.462729 |
| EMT05 | 595 nm | 0.062639 | 0.109488 | 0.181693 | 0.249231 | 0.314432 | 0.386 | 0.445348 | 0.520861 | 0.579047 | 0.644732 |
| EMT08 | 630 nm | 0.061339 | 0.333321 | 0.669098 | 1.017076 | 1.364458 | 1.71476 | 2.068693 | 2.417177 | 2.762461 | 3.103954 |
| EMT11 | 700 nm | 0.063163 | 0.672102 | 1.438606 | 2.246148 | 3.094262 | 3.963727 | 4.841787 | 5.735869 | 6.627411 | 7.536793 |
| EMT06 | 810 nm | 0.064003 | 5.039674 | 10.07217 | 15.12389 | 20.13012 | 25.11587 | 30.05372 | 34.94349 | 39.7839 | 44.54685 |
| EMT10 | 910 nm | 0.061244 | 8.622236 | 21.79082 | 36.3508 | 51.53181 | 66.99229 | 82.59837 | 98.20536 | 99.31124 | 99.204 |
| EMT12 | 970 nm | 0.058299 | 1.74861 | 3.618747 | 5.480242 | 7.279236 | 9.039397 | 10.75491 | 12.42833 | 14.0478 | 15.62556 |
| EMT09 | 1200 nm | 0.060993 | 0.144064 | 0.207686 | 0.278193 | 0.341296 | 0.399303 | 0.459564 | 0.505161 | 0.563484 | 0.609881 |
| EMT07 | 1450 nm | 0.060499 | 0.061202 | 0.05722 | 0.067252 | 0.063682 | 0.064367 | 0.059378 | 0.063574 | 0.063115 | 0.063467 |
| DET02 | 290 nm–370 nm | 0.000000% | 11.111111% | 22.222222% | 33.333333% | 44.444444% | 55.555556% | 66.666667% | 77.777778% | 88.888889% | 100.00000% |
| UV | | Level | Level | Level | Level | Level | Level | Level | Level | Level | Level |
| EMT01 | 355 nm | 0.021994 | 0.028858 | 0.031072 | 0.057691 | 0 | 0.013441 | 0.021827 | 0.013953 | 0.039548 | 0.039393 |
| EMT02 | 395 nm | 0.011295 | 0.00636 | 0.021809 | 0.043017 | 0.003415 | 0 | 0.002724 | 0.0045 | 0.005287 | 0.009859 |
| EMT03 | 468 nm | 0.013208 | 0 | 0.006425 | 0.027019 | 0.01812 | 0.019693 | 0.005162 | 0.001836 | 0.011259 | 0 |
| EMT04 | 574 nm | 0 | 0.017703 | 0 | 0 | 0.023961 | 0.042248 | 0.033689 | 0 | 0.015622 | 0.014311 |
| EMT05 | 595 nm | 0 | 0 | 0.027704 | 0.001138 | 0 | 0.020665 | 0.006431 | 0.01151 | 0.000352 | 0.002366 |
| EMT08 | 630 nm | 0 | 0.011712 | 0 | 0.001633 | 0.00146 | 0.015807 | 0 | 0.004262 | 0.019455 | 0.03041 |
| EMT11 | 700 nm | 0.043714 | 0 | 0.029427 | 0 | 0.032443 | 0.005931 | 0.017929 | 0.067866 | 0 | 0.026459 |
| EMT06 | 810 nm | 0.010467 | 0 | 0 | 0.059688 | 0.006503 | 0.004601 | 0.014287 | 0 | 0.013405 | 0.017643 |
| EMT10 | 910 nm | 0.019765 | 0.012863 | 0.020421 | 0.032282 | 0.031698 | 0.02349 | 0.046909 | 0 | 0.016254 | 0.025088 |
| EMT12 | 970 nm | 0.025553 | 0 | 0.002337 | 0.045049 | 0.020444 | 0 | 0 | 0 | 0 | 0.015688 |
| EMT09 | 1200 nm | 0.004649 | 0.012487 | 0.004715 | 0 | 0.002623 | 0.028557 | 0 | 0 | 0.022227 | 0 |
| EMT07 | 1450 nm | 0.018901 | 0 | 0.000644 | 0 | 0 | 0 | 0.026667 | 0 | 0 | 0 |
| DET03 | 900 nm–1700 nm | 0.000000% | 11.111111% | 22.222222% | 33.333333% | 44.444444% | 55.555556% | 66.666667% | 77.777778% | 88.888889% | 100.00000% |
| IR | | Level | Level | Level | Level | Level | Level | Level | Level | Level | Level |
| EMT01 | 355 nm | 0.06457 | 0.060815 | 0.062573 | 0.059919 | 0.064892 | 0.061214 | 0.064892 | 0.061488 | 0.067216 | 0.063497 |
| EMT02 | 395 nm | 0.062114 | 0.066596 | 0.058365 | 0.06749 | 0.07028 | 0.078565 | 0.076669 | 0.078636 | 0.076145 | 0.090021 |
| EMT03 | 468 nm | 0.064504 | 0.06485 | 0.077379 | 0.070912 | 0.067085 | 0.068498 | 0.075293 | 0.071484 | 0.068837 | 0.075489 |
| EMT04 | 574 nm | 0.070447 | 0.066322 | 0.064301 | 0.062335 | 0.069606 | 0.055891 | 0.06389 | 0.064927 | 0.068975 | 0.065094 |
| EMT05 | 595 nm | 0.058794 | 0.067383 | 0.065839 | 0.067735 | 0.066888 | 0.069302 | 0.061727 | 0.06771 | 0.064397 | 0.075436 |
| EMT08 | 630 nm | 0.063556 | 0.068402 | 0.077963 | 0.080287 | 0.086045 | 0.094241 | 0.109226 | 0.109899 | 0.120211 | 0.124097 |
| EMT11 | 700 nm | 0.063574 | 0.076061 | 0.066805 | 0.077599 | 0.080359 | 0.089073 | 0.082779 | 0.090879 | 0.101352 | 0.108248 |
| EMT06 | 810 nm | 0.05976 | 0.31004 | 0.584638 | 0.852442 | 1.114524 | 1.372612 | 1.63908 | 1.893068 | 2.15174 | 2.407092 |
| EMT10 | 910 nm | 0.07028 | 0.163674 | 0.33288 | 0.518751 | 0.704646 | 0.889969 | 1.086581 | 1.283753 | 1.474136 | 1.675999 |
| EMT12 | 970 nm | 0.062561 | 0.144297 | 0.236654 | 0.321221 | 0.402838 | 0.487274 | 0.571001 | 0.641406 | 0.718999 | 0.801307 |
| EMT07 | 1200 nm | 0.073469 | 1.10392 | 1.939607 | 2.661813 | 3.317201 | 3.916902 | 4.474426 | 5.00204 | 5.471999 | 5.94461 |
| EMT09 | 1450 nm | 0.057292 | 0.336027 | 0.562584 | 0.749552 | 0.916755 | 1.067948 | 1.209688 | 1.340222 | 1.455224 | 1.562441 |
| DET04 | 380 nm–1100 nm | 0.000000% | 11.111111% | 22.222222% | 33.333333% | 44.444444% | 55.555556% | 66.666667% | 77.777778% | 88.888889% | 100.00000% |
| Visible | | Level | Level | Level | Level | Level | Level | Level | Level | Level | Level |
| EMT01 | 355 nm | 0.066066 | 0.08412 | 0.12303 | 0.154209 | 0.184983 | 0.2047 | 0.22549 | 0.25003 | 0.26651 | 0.275475 |
| EMT02 | 395 nm | 0.06007 | 1.08074 | 2.444327 | 3.865803 | 5.281872 | 6.699795 | 8.082301 | 9.457321 | 10.80229 | 12.12678 |
| EMT03 | 468 nm | 0.057822 | 1.017255 | 1.692796 | 2.249885 | 2.752936 | 3.21405 | 3.652937 | 4.060948 | 4.455907 | 4.829085 |
| EMT04 | 574 nm | 0.067723 | 0.158608 | 0.277144 | 0.414687 | 0.53432 | 0.651723 | 0.76443 | 0.872368 | 0.969279 | 1.06839 |
| EMT05 | 595 nm | 0.062996 | 0.17342 | 0.297236 | 0.442475 | 0.581527 | 0.72642 | 0.856328 | 0.990033 | 1.11891 | 1.236749 |
| EMT08 | 630 nm | 0.061631 | 0.261527 | 0.489456 | 0.746107 | 0.989342 | 1.247329 | 1.480901 | 1.736665 | 1.985461 | 2.224404 |

| | | | | | | Cheese Aged 4 Years | | | | | |
|---|---|---|---|---|---|---|---|---|---|---|---|
| EMT11 | 700 nm | 0.060266 | 0.370103 | 0.746852 | 1.165587 | 1.586163 | 2.023363 | 2.462411 | 2.914888 | 3.361345 | 3.814608 |
| EMT06 | 810 nm | 0.059658 | 8.776213 | 17.60645 | 26.41887 | 35.19665 | 43.92451 | 52.57063 | 61.12662 | 69.59273 | 77.92224 |
| EMT10 | 910 nm | 0.057775 | 1.974601 | 4.9285 | 8.189858 | 11.58131 | 15.04376 | 18.53378 | 22.02733 | 25.5051 | 28.95976 |
| EMT12 | 970 nm | 0.052887 | 1.28848 | 2.658808 | 4.011351 | 5.333543 | 6.599951 | 7.851971 | 9.058977 | 10.24898 | 11.39642 |
| EMT07 | 1200 nm | 0.064403 | 0.131822 | 0.209636 | 0.271708 | 0.327957 | 0.37998 | 0.436407 | 0.489336 | 0.531107 | 0.58037 |
| EMT09 | 1450 nm | 0.060916 | 0.061798 | 0.062007 | 0.061762 | 0.063801 | 0.062752 | 0.065857 | 0.045395 | 0.052571 | 0.060791 |
| DET01 Visible | 380 nm–1100 nm | 0.000000% | 11.111111% | 22.222222% | 33.333333% | 44.444444% | 55.555556% | 66.666667% | 77.777778% | 88.888889% | 100.000000% |
| EMT01 | 355 nm | Level | Level | Level | Level | Level | Level | Level | Level | Level | Level |
| EMT01 | 355 nm | 0.056052 | 0.101703 | 0.135118 | 0.186878 | 0.210702 | 0.250584 | 0.272524 | 0.29915 | 0.326133 | 0.336927 |
| EMT02 | 395 nm | 0.061041 | 0.895274 | 2.023119 | 3.186649 | 4.360259 | 5.50772 | 6.658865 | 7.771058 | 8.880091 | 9.961058 |
| EMT03 | 468 nm | 0.062358 | 0.587469 | 0.958735 | 1.267666 | 1.548261 | 1.803941 | 2.046019 | 2.274758 | 2.499002 | 2.703059 |
| EMT04 | 574 nm | 0.060076 | 0.104713 | 0.149775 | 0.201112 | 0.248945 | 0.29422 | 0.342536 | 0.382042 | 0.426728 | 0.46047 |
| EMT05 | 595 nm | 0.064248 | 0.11043 | 0.183165 | 0.246751 | 0.318909 | 0.381327 | 0.456208 | 0.51347 | 0.584054 | 0.642544 |
| EMT08 | 630 nm | 0.061071 | 0.334078 | 0.669921 | 1.014751 | 1.373249 | 1.705456 | 2.058905 | 2.412868 | 2.761573 | 3.106112 |
| EMT11 | 700 nm | 0.066501 | 0.672358 | 1.439881 | 2.249313 | 3.10421 | 3.967566 | 4.849989 | 5.740303 | 6.646741 | 7.544512 |
| EMT06 | 810 nm | 0.061142 | 5.03831 | 10.0808 | 15.11896 | 20.13276 | 25.11316 | 30.05194 | 34.94421 | 39.77301 | 44.54461 |
| EMT10 | 910 nm | 0.054848 | 8.635164 | 21.8096 | 36.39229 | 51.56884 | 67.04584 | 82.66256 | 98.29667 | 99.32871 | 99.18813 |
| EMT12 | 970 nm | 0.059372 | 1.750195 | 3.626842 | 5.482227 | 7.289613 | 9.050287 | 10.76478 | 12.43937 | 14.06669 | 15.6521 |
| EMT07 | 1200 nm | 0.059694 | 0.140101 | 0.214195 | 0.282025 | 0.344276 | 0.400943 | 0.452673 | 0.509727 | 0.562155 | 0.608343 |
| EMT09 | 1450 nm | 0.058991 | 0.06249 | 0.05908 | 0.065446 | 0.061816 | 0.063843 | 0.061727 | 0.064641 | 0.052857 | 0.069296 |
| DET02 UV | 290 nm–370 nm | 0.000000% | 11.111111% | 22.222222% | 33.333333% | 44.444444% | 55.555556% | 66.666667% | 77.777778% | 88.888889% | 100.000000% |
| EMT01 | 355 nm | Level | Level | Level | Level | Level | Level | Level | Level | Level | Level |
| EMT01 | 355 nm | 0.010461 | 0.033635 | 0.022531 | 0.111461 | 0.011063 | 0.0453 | 0.020975 | 0.046057 | 0.02656 | 0.041109 |
| EMT02 | 395 nm | 0 | 0.018209 | 0.011414 | 0.013834 | 0.003135 | 0.005209 | 0.020367 | 0.011635 | 0.000054 | 0.024742 |
| EMT03 | 468 nm | 0 | 0 | 0.000173 | 0.006688 | 0.024945 | 0 | 0.012016 | 0 | 0.022733 | 0.03897 |
| EMT04 | 574 nm | 0.031501 | 0.011665 | 0.019693 | 0.003213 | 0.024432 | 0 | 0.023282 | 0 | 0.025785 | 0 |
| EMT05 | 595 nm | 0.027394 | 0.00543 | 0.024348 | 0 | 0.021857 | 0 | 0 | 0.001609 | 0.024021 | 0.002134 |
| EMT08 | 630 nm | 0.008708 | 0.031447 | 0.017345 | 0.014639 | 0.006717 | 0.047916 | 0 | 0 | 0.007343 | 0 |
| EMT11 | 700 nm | 0 | 0 | 0 | 0.001127 | 0.014395 | 0.005209 | 0.027472 | 0 | 0.001144 | 0.011432 |
| EMT06 | 810 nm | 0.029862 | 0.006825 | 0.028449 | 0.053948 | 0.013834 | 0.024539 | 0.002545 | 0.029153 | 0 | 0.027376 |
| EMT10 | 910 nm | 0 | 0.012958 | 0.0337 | 0.033271 | 0.038409 | 0.031781 | 0.046861 | 0.020242 | 0.000268 | 0.007135 |
| EMT12 | 970 nm | 0.009912 | 0.003546 | 0 | 0 | 0 | 0 | 0.02991 | 0 | 0 | 0 |
| EMT07 | 1200 nm | 0 | 0 | 0.022149 | 0.006425 | 0 | 0 | 0.00059 | 0 | 0.004435 | 0.002879 |
| EMT09 | 1450 nm | 0.006503 | 0.011289 | 0 | 0 | 0 | 0 | 0 | 0 | 0 | 0 |
| DET03 IR | 900 nm–1700 nm | 0.000000% | 11.111111% | 22.222222% | 33.333333% | 44.444444% | 55.555556% | 66.666667% | 77.777778% | 88.888889% | 100.000000% |
| EMT01 | 355 nm | Level | Level | Level | Level | Level | Level | Level | Level | Level | Level |
| EMT01 | 355 nm | 0.063562 | 0.065851 | 0.06485 | 0.065172 | 0.066251 | 0.063175 | 0.058836 | 0.061989 | 0.062668 | 0.060588 |
| EMT02 | 395 nm | 0.06963 | 0.062943 | 0.068891 | 0.074053 | 0.069135 | 0.077099 | 0.075668 | 0.064635 | 0.078666 | 0.089264 |
| EMT03 | 468 nm | 0.059503 | 0.069503 | 0.06395 | 0.073439 | 0.064838 | 0.076932 | 0.0642 | 0.078529 | 0.066561 | 0.077462 |
| EMT04 | 574 nm | 0.062233 | 0.067061 | 0.063515 | 0.064111 | 0.064367 | 0.064862 | 0.063342 | 0.069696 | 0.069278 | 0.063038 |
| EMT05 | 595 nm | 0.063872 | 0.063694 | 0.063527 | 0.064635 | 0.069559 | 0.068605 | 0.064981 | 0.069374 | 0.071859 | 0.069821 |
| EMT08 | 630 nm | 0.06477 | 0.060451 | 0.07565 | 0.080353 | 0.090706 | 0.091892 | 0.102109 | 0.114757 | 0.11977 | 0.116652 |
| EMT11 | 700 nm | 0.064576 | 0.066918 | 0.070649 | 0.076133 | 0.079954 | 0.084531 | 0.089186 | 0.09883 | 0.096792 | 0.108576 |
| EMT06 | 810 nm | 0.063461 | 0.318533 | 0.5813 | 0.851244 | 1.112682 | 1.373845 | 1.635689 | 1.898527 | 2.155954 | 2.413619 |
| EMT10 | 910 nm | 0.06541 | 0.171369 | 0.327069 | 0.515217 | 0.702572 | 0.892896 | 1.094669 | 1.277864 | 1.478744 | 1.673049 |
| EMT12 | 970 nm | 0.060558 | 0.149226 | 0.219953 | 0.32891 | 0.406826 | 0.490147 | 0.564575 | 0.645953 | 0.719059 | 0.798529 |
| EMT07 | 1200 nm | 0.069606 | 1.104605 | 1.94279 | 2.659273 | 3.315574 | 3.906429 | 4.477042 | 4.984862 | 5.483783 | 5.938846 |
| EMT09 | 1450 nm | 0.052607 | 0.339586 | 0.556254 | 0.750089 | 0.912857 | 1.070589 | 1.210618 | 1.333344 | 1.455319 | 1.565683 |
| DET04 Visible | 380 nm–1100 nm | 0.000000% | 11.111111% | 22.222222% | 33.333333% | 44.444444% | 55.555556% | 66.666667% | 77.777778% | 88.888889% | 100.000000% |
| EMT01 | 355 nm | 0.066572 | 0.088882 | 0.124693 | 0.142288 | 0.186938 | 0.201428 | 0.231886 | 0.242287 | 0.271314 | 0.275207 |

-continued

| | | | | | | | | | |
|---|---|---|---|---|---|---|---|---|---|
| EMT02 | 395 nm | 0.065094 | 1.076228 | 2.448619 | 3.864146 | 5.284584 | 6.698442 | 8.086694 | 9.459169 | 10.80203 | 12.12764 |
| EMT03 | 468 nm | 0.05753 | 1.017934 | 1.689297 | 2.273131 | 2.747685 | 3.212571 | 3.651864 | 4.061497 | 4.455287 | 4.829085 |
| EMT04 | 574 nm | 0.062054 | 0.163233 | 0.291336 | 0.414079 | 0.538164 | 0.64804 | 0.764823 | 0.869411 | 0.971699 | 1.065064 |
| EMT05 | 595 nm | 0.059038 | 0.168115 | 0.300229 | 0.447184 | 0.581878 | 0.727278 | 0.855404 | 0.994992 | 1.114035 | 1.242983 |
| EMT08 | 630 nm | 0.60135 | 0.258058 | 0.491411 | 0.743836 | 0.990045 | 1.243132 | 1.487672 | 1.740813 | 1.980865 | 2.227861 |
| EMT11 | 700 nm | 0.06358 | 0.368875 | 0.754094 | 1.164752 | 1.589292 | 2.02592 | 2.466518 | 2.914125 | 3.363383 | 3.814835 |
| EMT06 | 810 nm | 0.056279 | 8.77905 | 17.59409 | 26.42092 | 35.20453 | 43.92096 | 52.56033 | 61.12499 | 69.57473 | 77.90451 |
| EMT10 | 910 nm | 0.061673 | 1.978243 | 4.933066 | 8.186544 | 11.59468 | 15.05152 | 18.55284 | 22.01548 | 25.52163 | 28.98597 |
| EMT12 | 970 nm | 0.058085 | 1.291317 | 2.661956 | 4.018414 | 5.336911 | 6.605584 | 7.856972 | 9.070391 | 10.25642 | 11.40438 |
| EMT07 | 1200 nm | 0.062442 | 0.140101 | 0.207341 | 0.269651 | 0.330067 | 0.382924 | 0.440764 | 0.485003 | 0.530946 | 0.582004 |
| EMT09 | 1450 nm | 0.060743 | 0.061673 | 0.057805 | 0.060838 | 0.062567 | 0.059426 | 0.062126 | 0.05911 | 0.058275 | 0.053591 |

Example 3

Chromatic Profiles for Comparison of Tofu and Cheese

To evaluate whether ChromaID scanning could yield information about the protein content, tofu was chosen because it looks similar to that of cheese on visual inspection. The ChromaID data has revealed that different intensity, as well as the change of relative intensity, at 355 nm (with EMT01) and 700 nm (with EMT11) as compared to that at 910 nm (with EMT10) and 970 nm (with EMT12). It can be seen that Tofu and cheese exhibit a different reaction to scanning, primarily at 355 nm and 700 nm wavelengths.

| | | | 0.000000% | 11.111111% | 22.222222% | 33.333333% | 44.444444% | 55.555556% | 66.666667% | 77.777778% | 88.888889% | 100.000000% |
|---|---|---|---|---|---|---|---|---|---|---|---|---|
| | | | | | | | Tofu | | | | | |
| DET01 Visible | | 380 nm–1100 nm | Level | Level | Level | Level | Level | Level | Level | Level | Level | Level |
| EMT01 | | 355 nm | 0.065911 | 0.079852 | 0.107825 | 0.122184 | 0.148821 | 0.163788 | 0.177097 | 0.186902 | 0.205869 | 0.207245 |
| EMT02 | | 395 nm | 0.064248 | 0.646854 | 1.438201 | 2.254284 | 3.068537 | 3.878957 | 4.673094 | 5.460603 | 6.229145 | 6.99153 |
| EMT03 | | 468 nm | 0.058866 | 0.50118 | 0.801134 | 1.061827 | 1.287782 | 1.496887 | 1.691252 | 1.881123 | 2.049196 | 2.22525 |
| EMT04 | | 574 nm | 0.065494 | 0.11825 | 0.180101 | 0.23973 | 0.302923 | 0.361466 | 0.419724 | 0.4798 | 0.525242 | 0.577235 |
| EMT05 | | 595 nm | 0.061405 | 0.137281 | 0.214601 | 0.296491 | 0.390202 | 0.483477 | 0.572085 | 0.657344 | 0.737786 | 0.816882 |
| EMT08 | | 630 nm | 0.059915 | 0.387818 | 0.767773 | 1.182264 | 1.592517 | 2.008271 | 2.403373 | 2.82051 | 3.220594 | 3.626848 |
| EMT11 | | 700 nm | 0.062805 | 0.806499 | 1.729912 | 2.721429 | 3.750956 | 4.809052 | 5.873186 | 6.955755 | 8.054692 | 9.153605 |
| EMT06 | | 810 nm | 0.063753 | 8.224005 | 16.48362 | 24.72908 | 32.94236 | 41.08161 | 49.19017 | 57.19586 | 65.12972 | 72.94718 |
| EMT10 | | 910 nm | 0.064141 | 8.28271 | 20.94807 | 34.9631 | 49.55446 | 64.44509 | 79.45185 | 94.48635 | 99.38252 | 99.20299 |
| EMT12 | | 970 nm | 0.066954 | 2.268237 | 4.728532 | 7.156683 | 9.531439 | 11.82562 | 14.07558 | 16.25741 | 18.38145 | 20.44408 |
| EMT09 | | 1200 nm | 0.063914 | 0.169557 | 0.268239 | 0.357175 | 0.428021 | 0.510937 | 0.582641 | 0.653815 | 0.718629 | 0.788677 |
| | | 1450 nm | 0.062227 | 0.064141 | 0.062275 | 0.064522 | 0.064588 | 0.063628 | 0.067031 | 0.065243 | 0.065237 | 0.065178 |
| DET02 UV | | 290 nm–370 nm | 0.000000% | 11.111111% | 22.222222% | 33.333333% | 44.444444% | 55.555556% | 66.666667% | 77.777778% | 88.888889% | 100.000000% |
| | | | Level | Level | Level | Level | Level | Level | Level | Level | Level | Level |
| EMT01 | | 355 nm | 0.022483 | 0.006294 | 0.030828 | 0 | 0.018346 | 0.017619 | 0.041252 | 0 | 0.004768 | 0.035071 |
| EMT02 | | 395 nm | 0.008762 | 0.007981 | 0 | 0.012153 | 0 | 0.018281 | 0.021631 | 0.03078 | 0 | 0.009459 |
| EMT03 | | 468 nm | 0.005281 | 0.03733 | 0.00034 | 0.007784 | 0 | 0.01449 | 0 | 0.030249 | 0.019753 | 0.022811 |
| EMT04 | | 574 nm | 0 | 0.024194 | 0.009787 | 0 | 0.030363 | 0.027817 | 0 | 0 | 0.029302 | 0.02445 |
| EMT05 | | 595 nm | 0.030702 | 0 | 0.001431 | 0.040084 | 0.013083 | 0 | 0 | 0.019658 | 0.004697 | 0.007629 |
| EMT08 | | 630 nm | 0 | 0.018322 | 0.028127 | 0 | 0.013584 | 0 | 0.026786 | 0.023806 | 0.015461 | 0.004667 |
| EMT11 | | 700 nm | 0.015748 | 0 | 0 | 0 | 0.00909 | 0.001049 | 0.002348 | 0.00124 | 0.005871 | 0 |
| EMT06 | | 810 nm | 0.063562 | 0 | 0 | 0.017077 | 0.03404 | 0.01992 | 0.039363 | 0.007415 | 0.010347 | 0.045627 |
| EMT10 | | 910 nm | 0.016183 | 0 | 0.022018 | 0.012147 | 0.051969 | 0.009936 | 0.029427 | 0.045818 | 0.022018 | 0 |
| EMT12 | | 970 nm | 0.001049 | 0 | 0 | 0.007576 | 0 | 0.005013 | 0 | 0.003409 | 0 | 0.022542 |
| EMT09 | | 1200 nm | 0.001889 | 0.016779 | 0 | 0.001675 | 0.004619 | 0 | 0 | 0 | 0 | 0.0094 |
| DET03 IR | | 900 nm–1700 nm | 0.000000% | 11.111111% | 22.222222% | 33.333333% | 44.444444% | 55.555556% | 66.666667% | 77.777778% | 88.888889% | 100.000000% |
| | | | Level | Level | Level | Level | Level | Level | Level | Level | Level | Level |
| EMT01 | | 355 nm | 0.063318 | 0.062901 | 0.062501 | 0.068402 | 0.06116 | 0.063932 | 0.058526 | 0.065172 | 0.062108 | 0.071758 |
| EMT02 | | 395 nm | 0.059342 | 0.068998 | 0.064844 | 0.076175 | 0.063837 | 0.066286 | 0.068772 | 0.07726 | 0.075954 | 0.080526 |
| EMT03 | | 468 nm | 0.06274 | 0.064105 | 0.067437 | 0.066727 | 0.071579 | 0.068659 | 0.072348 | 0.067103 | 0.07652 | 0.070161 |
| EMT04 | | 574 nm | 0.064278 | 0.062633 | 0.067377 | 0.05154 | 0.067723 | 0.066531 | 0.076777 | 0.068438 | 0.067711 | 0.068295 |
| EMT05 | | 595 nm | 0.063473 | 0.065619 | 0.07357 | 0.066537 | 0.065392 | 0.070447 | 0.072062 | 0.075114 | 0.071442 | 0.068212 |
| EMT08 | | 630 nm | 0.064164 | 0.068367 | 0.070268 | 0.083894 | 0.091928 | 0.095415 | 0.104898 | 0.107515 | 0.120682 | 0.119495 |
| EMT11 | | 700 nm | 0.06144 | 0.069207 | 0.07655 | 0.08319 | 0.096494 | 0.103146 | 0.10199 | 0.116962 | 0.121695 | 0.134838 |
| EMT06 | | 810 nm | 0.062585 | 0.376004 | 0.683731 | 1.000381 | 1.309222 | 1.623583 | 1.935452 | 2.248531 | 2.547568 | 2.860481 |
| EMT10 | | 910 nm | 0.066853 | 0.21897 | 0.470161 | 0.738669 | 1.019007 | 1.302725 | 1.592386 | 1.880026 | 2.169252 | 2.463782 |
| EMT12 | | 970 nm | 0.068122 | 0.185782 | 0.318092 | 0.46078 | 0.591606 | 0.717968 | 0.833184 | 0.951976 | 1.0656 | 1.184195 |
| EMT07 | | 1200 nm | 0.05765 | 0.971991 | 1.685256 | 2.314133 | 2.869022 | 3.392935 | 3.869468 | 4.318965 | 4.735619 | 5.144227 |
| EMT09 | | 1450 nm | 0.071645 | 0.248128 | 0.403369 | 0.521153 | 0.64556 | 0.747126 | 0.846618 | 0.929076 | 1.011163 | 1.085287 |
| DET04 Visible | | 380 nm–1100 nm | 0.000000% | 11.111111% | 22.222222% | 33.333333% | 44.444444% | 55.555556% | 66.666667% | 77.777778% | 88.888889% | 100.000000% |
| | | | Level | Level | Level | Level | Level | Level | Level | Level | Level | Level |
| EMT01 | | 355 nm | 0.063556 | 0.07602 | 0.096953 | 0.116557 | 0.126767 | 0.146389 | 0.151068 | 0.167245 | 0.175005 | 0.186807 |
| EMT02 | | 395 nm | 0.063002 | 0.792003 | 1.781213 | 2.800656 | 3.826815 | 4.834551 | 5.835605 | 6.808168 | 7.784177 | 8.728809 |
| EMT03 | | 468 nm | 0.073516 | 0.831676 | 1.376748 | 1.816678 | 2.222258 | 2.585757 | 2.93597 | 3.259486 | 3.572578 | 3.868312 |
| EMT04 | | 574 nm | 0.064182 | 0.167573 | 0.29484 | 0.420445 | 0.530714 | 0.65968 | 0.768727 | 0.880176 | 0.978959 | 1.082689 |
| EMT05 | | 595 nm | 0.060225 | 0.168324 | 0.300586 | 0.442278 | 0.577277 | 0.708854 | 0.845629 | 0.976771 | 1.10299 | 1.224727 |
| EMT08 | | 630 nm | 0.064039 | 0.315505 | 0.622797 | 0.938201 | 1.261056 | 1.577515 | 1.909125 | 2.223391 | 2.541644 | 2.837479 |

| | | | | | | | | | |
|---|---|---|---|---|---|---|---|---|---|
| EMT11 | 700 nm | 0.065809 | 0.531423 | 1.102156 | 1.715589 | 2.360058 | 3.013689 | 3.679067 | 4.350722 | 5.035896 | 5.71661 |
| EMT06 | 810 nm | 0.066096 | 11.55753 | 23.19987 | 34.82193 | 46.39857 | 57.8724 | 69.28055 | 80.56565 | 91.71161 | 99.23241 |
| EMT10 | 910 nm | 0.061041 | 3.193182 | 8.015282 | 13.35672 | 18.91263 | 24.58988 | 30.29432 | 36.01883 | 41.71051 | 47.38144 |
| EMT12 | 970 nm | 0.056833 | 1.796293 | 3.723312 | 5.622113 | 7.498056 | 9.289265 | 11.05481 | 12.7596 | 14.42462 | 16.04729 |
| EMT07 | 1200 nm | 0.064427 | 0.167578 | 0.255132 | 0.337911 | 0.41182 | 0.486362 | 0.55573 | 0.620538 | 0.680232 | 0.742114 |
| EMT09 | 1450 nm | 0.062966 | 0.061578 | 0.064987 | 0.05911 | 0.08049 | 0.061661 | 0.06178 | 0.064784 | 0.061786 | 0.070071 |

Mild Cheddar Cheese

| | | | | | | | | | | | |
|---|---|---|---|---|---|---|---|---|---|---|---|
| DET01 | 380 nm–1100 nm | 0.000000% | 11.11111% | 22.22222% | 33.33333% | 44.44444% | 55.55556% | 66.66667% | 77.77778% | 88.88889% | 100.00000% |
| Visible | | Level | Level | Level | Level | Level | Level | Level | Level | Level | Level |
| EMT01 | 355 nm | 0.090975 | 0.100636 | 0.112355 | 0.123978 | 0.134522 | 0.142771 | 0.150895 | 0.160056 | 0.166851 | 0.177628 |
| EMT02 | 395 nm | 0.090104 | 0.328296 | 0.654703 | 0.991649 | 1.326537 | 1.662111 | 1.988995 | 2.315552 | 2.631152 | 2.945882 |
| EMT03 | 468 nm | 0.088662 | 0.202572 | 0.278986 | 0.347966 | 0.405145 | 0.462639 | 0.516039 | 0.562751 | 0.610727 | 0.652266 |
| EMT04 | 574 nm | 0.09051 | 0.119877 | 0.159878 | 0.192189 | 0.240165 | 0.272888 | 0.314426 | 0.346833 | 0.379664 | 0.409871 |
| EMT05 | 595 nm | 0.088328 | 0.141978 | 0.198215 | 0.267434 | 0.322777 | 0.395656 | 0.450981 | 0.517011 | 0.569814 | 0.651598 |
| EMT08 | 630 nm | 0.089097 | 0.362837 | 0.686336 | 1.030904 | 1.376009 | 1.724309 | 2.068073 | 2.408111 | 2.737373 | 3.088874 |
| EMT11 | 700 nm | 0.090456 | 0.780839 | 1.631475 | 2.551115 | 3.496379 | 4.475195 | 5.459244 | 6.465853 | 7.472087 | 8.490259 |
| EMT06 | 810 nm | 0.086492 | 6.238884 | 12.47267 | 18.6899 | 24.88083 | 31.0371 | 37.14385 | 43.17348 | 49.15174 | 55.04374 |
| EMT10 | 910 nm | 0.089228 | 7.935996 | 20.03017 | 33.39232 | 47.33068 | 61.53771 | 75.86035 | 90.20154 | 99.37103 | 99.206 |
| EMT12 | 970 nm | 0.09644 | 1.924616 | 3.968209 | 5.983526 | 7.952572 | 9.858824 | 11.73068 | 13.53682 | 15.31089 | 17.02198 |
| EMT07 | 1200 nm | 0.090468 | 0.171536 | 0.248063 | 0.319088 | 0.382113 | 0.440109 | 0.500464 | 0.560117 | 0.609964 | 0.667864 |
| EMT09 | 1450 nm | 0.090688 | 0.088757 | 0.091743 | 0.092983 | 0.095987 | 0.092661 | 0.094801 | 0.09191 | 0.091636 | 0.089377 |
| DET02 | 290 nm–370 nm | 0.000000% | 11.11111% | 22.22222% | 33.33333% | 44.44444% | 55.55556% | 66.66667% | 77.77778% | 88.88889% | 100.00000% |
| UV | | Level | Level | Level | Level | Level | Level | Level | Level | Level | Level |
| EMT01 | 355 nm | 0 | 0.012106 | 0.008857 | 0.035 | 0.010842 | 0.020832 | 0.027293 | 0.022161 | 0.004709 | 0.007945 |
| EMT02 | 395 nm | 0.032628 | 0 | 0.024092 | 0.017881 | 0.01874 | 0.008017 | 0 | 0 | 0 | 0 |
| EMT03 | 468 nm | 0 | 0.030118 | 0 | 0 | 0 | 0.016224 | 0 | 0.028235 | 0.001711 | 0.000465 |
| EMT04 | 574 nm | 0.011116 | 0 | 0.028402 | 0 | 0.020057 | 0.012147 | 0 | 0 | 0.003165 | 0.010103 |
| EMT05 | 595 nm | 0.001347 | 0.025296 | 0 | 0.03078 | 0.000125 | 0.007498 | 0 | 0 | 0.011629 | 0.004691 |
| EMT08 | 630 nm | 0.021434 | 0 | 0.024813 | 0 | 0.015998 | 0 | 0.001031 | 0 | 0 | 0.011182 |
| EMT11 | 700 nm | 0.033093 | 0.015801 | 0 | 0.031215 | 0 | 0.020373 | 0 | 0.026315 | 0 | 0 |
| EMT06 | 810 nm | 0.033563 | 0 | 0.02833 | 0.000376 | 0.023204 | 0.016028 | 0 | 0.001764 | 0 | 0.029498 |
| EMT10 | 910 nm | 0.027061 | 0.031525 | 0.034606 | 0.024176 | 0.037169 | 0.030959 | 0 | 0 | 0.001277 | 0.015461 |
| EMT12 | 970 nm | 0.010264 | 0 | 0.004232 | 0.017726 | 0.035733 | 0.020719 | 0 | 0.005782 | 0.022954 | 0.019717 |
| EMT07 | 1200 nm | 0 | 0.023663 | 0.007057 | 0.021267 | 0 | 0.008923 | 0 | 0 | 0 | 0 |
| EMT09 | 1450 nm | 0 | 0.011706 | 0.019169 | 0.019169 | 0.013381 | 0.002098 | 0 | 0 | 0 | 0 |
| DET03 | 900 nm–1700 nm | 0.000000% | 11.11111% | 22.22222% | 33.33333% | 44.44444% | 55.55556% | 66.66667% | 77.77778% | 88.88889% | 100.00000% |
| IR | | Level | Level | Level | Level | Level | Level | Level | Level | Level | Level |
| EMT01 | 355 nm | 0.064003 | 0.069076 | 0.068384 | 0.07003 | 0.067264 | 0.057602 | 0.066811 | 0.063849 | 0.065643 | 0.06541 |
| EMT02 | 395 nm | 0.066602 | 0.068074 | 0.065053 | 0.071055 | 0.065237 | 0.070006 | 0.067377 | 0.07239 | 0.070667 | 0.072807 |
| EMT03 | 468 nm | 0.066036 | 0.066036 | 0.069702 | 0.064838 | 0.070751 | 0.068092 | 0.071847 | 0.062048 | 0.070399 | 0.06721 |
| EMT04 | 574 nm | 0.068766 | 0.065964 | 0.06637 | 0.064504 | 0.062418 | 0.070101 | 0.069803 | 0.071788 | 0.051594 | 0.071704 |
| EMT05 | 595 nm | 0.063956 | 0.0709 | 0.065613 | 0.078177 | 0.067538 | 0.067759 | 0.07447 | 0.069451 | 0.07782 | 0.063485 |
| EMT08 | 630 nm | 0.062888 | 0.067592 | 0.068867 | 0.084376 | 0.088859 | 0.098026 | 0.102288 | 0.10891 | 0.114572 | 0.123745 |
| EMT11 | 700 nm | 0.062168 | 0.070834 | 0.07301 | 0.081277 | 0.095564 | 0.091779 | 0.09864 | 0.103498 | 0.117743 | 0.114745 |
| EMT06 | 810 nm | 0.06541 | 0.337374 | 0.618541 | 0.897372 | 1.174182 | 1.455742 | 1.732201 | 2.009767 | 2.279747 | 2.557892 |
| EMT10 | 910 nm | 0.068301 | 0.183684 | 0.373417 | 0.583065 | 0.787216 | 1.018071 | 1.237053 | 1.463759 | 1.679498 | 1.906109 |
| EMT12 | 970 nm | 0.06761 | 0.14919 | 0.250614 | 0.353158 | 0.444323 | 0.53556 | 0.617003 | 0.704855 | 0.781882 | 0.870574 |
| EMT07 | 1200 nm | 0.066072 | 0.952756 | 1.647717 | 2.260965 | 2.809334 | 3.30953 | 3.780622 | 4.214538 | 4.627252 | 5.015499 |
| EMT09 | 1450 nm | 0.070804 | 0.24156 | 0.390202 | 0.513876 | 0.628108 | 0.723624 | 0.822765 | 0.901401 | 0.984824 | 1.056576 |
| DET04 | 380 nm–1100 nm | 0.000000% | 11.11111% | 22.22222% | 33.33333% | 44.44444% | 55.55556% | 66.66667% | 77.77778% | 88.88889% | 100.00000% |
| Visible | | Level | Level | Level | Level | Level | Level | Level | Level | Level | Level |
| EMT01 | 355 nm | 0.094169 | 0.103343 | 0.107318 | 0.122976 | 0.129241 | 0.142062 | 0.141996 | 0.152606 | 0.154072 | 0.167614 |

-continued

| | | | | | | | | | |
|---|---|---|---|---|---|---|---|---|---|
| EMT02 | 395 nm | 0.088167 | 0.556648 | 1.198721 | 1.872385 | 2.544451 | 3.207422 | 3.867424 | 4.51271 | 5.162043 | 5.791629 |
| EMT03 | 468 nm | 0.097561 | 0.642133 | 1.031625 | 1.346767 | 1.641172 | 1.904714 | 2.155191 | 2.393383 | 2.618194 | 2.841431 |
| EMT04 | 574 nm | 0.089288 | 0.190777 | 0.288385 | 0.402194 | 0.49904 | 0.604045 | 0.699085 | 0.79304 | 0.877923 | 0.964177 |
| EMT05 | 595 nm | 0.099409 | 0.177515 | 0.291991 | 0.405991 | 0.527394 | 0.639725 | 0.755632 | 0.863856 | 0.971407 | 1.071781 |
| EMT08 | 630 nm | 0.088722 | 0.290298 | 0.529063 | 0.78162 | 1.038307 | 1.288879 | 1.54835 | 1.791555 | 2.038074 | 2.286887 |
| EMT11 | 700 nm | 0.093597 | 0.456125 | 0.907761 | 1.388544 | 1.899356 | 2.408892 | 2.932692 | 3.458101 | 3.992045 | 4.527802 |
| EMT06 | 810 nm | 0.090665 | 9.809292 | 19.64786 | 29.47837 | 39.26186 | 48.97938 | 58.62526 | 68.15915 | 77.59209 | 86.88771 |
| EMT10 | 910 nm | 0.091064 | 2.379072 | 5.885083 | 9.779794 | 13.82585 | 17.95943 | 22.11616 | 26.27039 | 30.40532 | 34.52336 |
| EMT12 | 970 nm | 0.090086 | 1.454866 | 2.977664 | 4.485888 | 5.948359 | 7.365078 | 8.749545 | 10.09951 | 11.41017 | 12.68819 |
| EMT07 | 1200 nm | 0.089794 | 0.171804 | 0.240719 | 0.306571 | 0.363052 | 0.420702 | 0.472128 | 0.527436 | 0.560331 | 0.616896 |
| EMT09 | 1450 nm | 0.093085 | 0.086373 | 0.09259 | 0.088161 | 0.090802 | 0.088596 | 0.092042 | 0.096083 | 0.088686 | 0.09625 |

Example 4

Chromatic Profile for Butter

To evaluate whether ChromaID scanning could yield a chromatic profile for butter, the surface of a sample of butter was scanned as above. The ChromaID data revealed different intensity, as well as the change of relative intensity, at different interrogation wavelengths than either Tofu or cheese. Thus, a distinctive spectral pattern is evident for the different dairy products tested.

| | | Butter | | | | | | | | | |
|---|---|---|---|---|---|---|---|---|---|---|---|
| DET01 Visible | 380 nm–1100 nm | 0.000000% | 11.111111% | 22.222222% | 33.333333% | 44.444444% | 55.555556% | 66.666667% | 77.777778% | 88.888889% | 100.00000% |
| | | Level | Level | Level | Level | Level | Level | Level | Level | Level | Level |
| EMT01 | 355 nm | 0.08238 | 0.101203 | 0.145471 | 0.17727 | 0.202113 | 0.228173 | 0.243449 | 0.271767 | 0.28736 | 0.298995 |
| EMT02 | 395 nm | 0.083286 | 0.8618 | 1.906365 | 2.997387 | 4.080022 | 5.154175 | 6.213278 | 7.252503 | 8.280177 | 9.290028 |
| EMT03 | 468 nm | 0.082392 | 0.513899 | 0.817734 | 1.068032 | 1.298267 | 1.50255 | 1.70086 | 1.882959 | 2.059508 | 2.22953 |
| EMT04 | 574 nm | 0.084305 | 0.141114 | 0.223565 | 0.300658 | 0.375742 | 0.452232 | 0.519013 | 0.578964 | 0.635797 | 0.704068 |
| EMT05 | 595 nm | 0.082392 | 0.165856 | 0.256842 | 0.367814 | 0.473839 | 0.580442 | 0.68357 | 0.782138 | 0.878173 | 0.971902 |
| EMT08 | 630 nm | 0.083613 | 0.433421 | 0.868535 | 1.319879 | 1.7721 | 2.225435 | 2.683014 | 3.125775 | 3.580696 | 4.021013 |
| EMT11 | 700 nm | 0.082344 | 0.864613 | 1.825065 | 2.861405 | 3.924108 | 5.037523 | 6.14757 | 7.286049 | 8.426572 | 9.570486 |
| EMT06 | 810 nm | 0.083739 | 8.583326 | 17.19859 | 25.78616 | 34.35121 | 42.85078 | 51.28737 | 59.62564 | 67.88469 | 76.00705 |
| EMT10 | 910 nm | 0.083721 | 8.377338 | 21.14003 | 35.24666 | 49.94447 | 64.93582 | 80.04576 | 95.17361 | 99.34768 | 99.21017 |
| EMT12 | 970 nm | 0.088161 | 2.561945 | 5.322922 | 8.043719 | 10.70399 | 13.27593 | 15.805 | 18.255 | 20.64893 | 22.97905 |
| EMT09 | 1200 nm | 0.084776 | 0.205916 | 0.31659 | 0.417864 | 0.507081 | 0.597328 | 0.681174 | 0.762594 | 0.837308 | 0.913864 |
| | 1450 nm | 0.088227 | 0.083327 | 0.086117 | 0.083983 | 0.083655 | 0.082278 | 0.090575 | 0.079626 | 0.086063 | 0.086635 |
| DET02 UV | 290 nm–370 nm | 0.000000% | 11.111111% | 22.222222% | 33.333333% | 44.444444% | 55.555556% | 66.666667% | 77.777778% | 88.888889% | 100.00000% |
| | | Level | Level | Level | Level | Level | Level | Level | Level | Level | Level |
| EMT01 | 355 nm | 0.00267 | 0 | 0.014973 | 0 | 0.02436 | 0.024843 | 0.007069 | 0.031632 | 0.009477 | 0.026447 |
| EMT02 | 395 nm | 0.047749 | 0.007337 | 0.024188 | 0.018948 | 0 | 0.021845 | 0 | 0 | 0.013447 | 0.00329 |
| EMT03 | 468 nm | 0.069225 | 0.040096 | 0.011146 | 0.016832 | 0.016904 | 0 | 0.001115 | 0 | 0 | 0.017834 |
| EMT04 | 574 nm | 0.005913 | 0.00248 | 0.037563 | 0.028735 | 0.019222 | 0.003666 | 0 | 0.006205 | 0.011206 | 0 |
| EMT05 | 595 nm | 0.046444 | 0 | 0.008494 | 0.04611 | 0 | 0 | 0.016636 | 0.011307 | 0.008947 | 0.026917 |
| EMT08 | 630 nm | 0 | 0.035459 | 0 | 0 | 0.024277 | 0.022316 | 0 | 0.025719 | 0.00723 | 0.010383 |
| EMT11 | 700 nm | 0.006545 | 0.017333 | 0.000143 | 0.010514 | 0.030875 | 0 | 0.01089 | 0 | 0.040603 | 0.019038 |
| EMT06 | 810 nm | 0.034779 | 0 | 0.021261 | 0.076813 | 0.055081 | 0.029862 | 0.029957 | 0.007141 | 0.031453 | 0.058568 |
| EMT10 | 910 nm | 0.016862 | 0 | 0 | 0.019723 | 0.000918 | 0.02504 | 0 | 0.002074 | 0 | 0.010473 |
| EMT12 | 970 nm | 0.021136 | 0 | 0 | 0.022322 | 0.010091 | 0.049591 | 0.004274 | 0 | 0 | 0 |
| EMT07 | 1200 nm | 0.042087 | 0 | 0.008726 | 0 | 0 | 0 | 0 | 0.062466 | 0.020981 | 0 |
| EMT09 | 1450 nm | 0 | | | | | | | | | |
| DET03 IR | 900 nm–1700 nm | 0.000000% | 11.111111% | 22.222222% | 33.333333% | 44.444444% | 55.555556% | 66.666667% | 77.777778% | 88.888889% | 100.00000% |
| | | Level | Level | Level | Level | Level | Level | Level | Level | Level | Level |
| EMT01 | 355 nm | 0.054967 | 0.068307 | 0.062966 | 0.066918 | 0.064331 | 0.060081 | 0.062293 | 0.069058 | 0.065196 | 0.058627 |
| EMT02 | 395 nm | 0.061011 | 0.060183 | 0.072694 | 0.068736 | 0.072056 | 0.075287 | 0.075406 | 0.092387 | 0.087857 | 0.084722 |
| EMT03 | 468 nm | 0.060016 | 0.065506 | 0.063616 | 0.071371 | 0.065601 | 0.066412 | 0.071675 | 0.067788 | 0.072527 | 0.078529 |
| EMT04 | 574 nm | 0.063944 | 0.068772 | 0.062627 | 0.060332 | 0.066733 | 0.064182 | 0.063115 | 0.072145 | 0.067133 | 0.069427 |
| EMT05 | 595 nm | 0.072098 | 0.06544 | 0.070268 | 0.068676 | 0.066328 | 0.071716 | 0.070721 | 0.070751 | 0.07332 | 0.073528 |
| EMT08 | 630 nm | 0.062442 | 0.067198 | 0.072289 | 0.089127 | 0.094169 | 0.097114 | 0.108391 | 0.110471 | 0.122684 | 0.12455 |
| EMT11 | 700 nm | 0.065935 | 0.072217 | 0.076401 | 0.082564 | 0.097811 | 0.1019 | 0.115973 | 0.123489 | 0.129664 | 0.13811 |
| EMT06 | 810 nm | 0.034779 | 0.379467 | 0.704992 | 1.00593 | 1.337147 | 1.648843 | 1.974243 | 2.294839 | 2.599889 | 2.918697 |
| EMT10 | 910 nm | 0.064963 | 0.231195 | 0.476354 | 0.757301 | 1.036555 | 1.337618 | 1.626855 | 1.927883 | 2.214724 | 2.514541 |
| EMT12 | 970 nm | 0.059354 | 0.205517 | 0.370693 | 0.529563 | 0.684601 | 0.8376 | 0.974536 | 1.118171 | 1.259112 | 1.392686 |
| EMT07 | 1200 nm | 0.047809 | 0.994253 | 1.731497 | 2.376646 | 2.954734 | 3.485859 | 3.986025 | 4.450411 | 4.883361 | 5.293137 |
| EMT09 | 1450 nm | 0.061804 | 0.330341 | 0.529677 | 0.72934 | 0.901294 | 1.048017 | 1.184958 | 1.311427 | 1.422447 | 1.536894 |
| DET04 | 380 nm–1100 nm | 0.000000% | 11.111111% | 22.222222% | 33.333333% | 44.444444% | 55.555556% | 66.666667% | 77.777778% | 88.888889% | 100.00000% |
| Visible | | Level | Level | Level | Level | Level | Level | Level | Level | Level | Level |
| EMT01 | 355 nm | 0.08378 | 0.107789 | 0.130588 | 0.161642 | 0.173694 | 0.200176 | 0.217491 | 0.229818 | 0.247598 | 0.26021 |
| EMT02 | 395 nm | 0.082523 | 0.997496 | 2.231914 | 3.506232 | 4.791749 | 6.047077 | 7.300389 | 8.523715 | 9.728254 | 10.9121 |
| EMT03 | 468 nm | 0.082785 | 0.82984 | 1.368314 | 1.811206 | 2.205914 | 2.573878 | 2.910573 | 3.241021 | 3.549761 | 3.838098 |
| EMT04 | 574 nm | 0.080913 | 0.200689 | 0.334108 | 0.477189 | 0.610727 | 0.741804 | 0.867814 | 0.985319 | 1.098073 | 1.208395 |
| EMT05 | 595 nm | 0.076026 | 0.197262 | 0.348884 | 0.499171 | 0.658077 | 0.807518 | 0.951982 | 1.02948 | 1.242071 | 1.371986 |
| EMT08 | 630 nm | 0.084156 | 0.374085 | 0.728124 | 1.084995 | 1.460499 | 1.828402 | 2.198261 | 2.560532 | 2.928764 | 3.279865 |

-continued

| | | | | | Butter | | | | | |
|---|---|---|---|---|---|---|---|---|---|---|
| EMT11 | 700 nm | 0.086176 | 0.585032 | 1.212829 | 1.886034 | 2.578861 | 3.280992 | 4.011679 | 4.73739 | 5.473173 | 6.217677 |
| EMT06 | 810 nm | 0.084221 | 11.96618 | 24.01669 | 36.05007 | 48.01958 | 59.91634 | 71.70643 | 83.3799 | 94.90747 | 99.14553 |
| EMT10 | 910 nm | 0.077826 | 3.323138 | 8.309574 | 13.82488 | 19.56643 | 25.41061 | 31.31112 | 37.21066 | 43.09061 | 48.92315 |
| EMT12 | 970 nm | 0.079751 | 2.09375 | 4.324973 | 6.536913 | 8.692462 | 10.77765 | 12.80934 | 14.79344 | 16.72026 | 18.60204 |
| EMT07 | 1200 nm | 0.081033 | 0.204688 | 0.297785 | 0.400144 | 0.486952 | 0.57314 | 0.650334 | 0.726307 | 0.799072 | 0.870538 |
| EMT09 | 1450 nm | 0.086832 | 0.087208 | 0.081742 | 0.084484 | 0.081056 | 0.084275 | 0.084853 | 0.085109 | 0.07838 | 0.082445 |

Additional scans were taken of fat free (skim) milk, 1% reduced fat milk, 2% reduced fat milk, and whole milk for plotting, with a single visible light detector. (DET01 Visible). The scan data are plotted (10 firings for each of the LEDs). The plots of the detected reflected light are shown in FIGS. 9-12, for skim milk, 1% reduced fat milk, 2% reduced fat milk, and whole milk, respectively. A plot of the reflected light detected at 810 nm, 910 nm, and 970 nm illustrates a change in slope and are more compact as the fat content in the milk decreases. The data for these scans are also provided below in tabular form below. Thus, the chromatic profiles allow discrimination of fat content in the four different milk products. DET01 had a response range of 380 nm-1100 nm. The range indication is truncated in the respective displayed tables.

Skim Milk Scan Data

| | | 0.000000% Level | 11.111111% Level | 22.222222% Level | 33.333333% Level | 44.444444% Level | 55.555556% Level | 66.666667% Level | 77.777778% Level | 88.888889% Level | 100.00000% Level |
|---|---|---|---|---|---|---|---|---|---|---|---|
| DET01 Visible | 380 nm–1100 nm | 1.89901 | 2.180606 | 2.623612 | 2.992821 | 3.427297 | 3.820926 | 4.222882 | 4.653472 | 5.004281 | 5.472661 |
| EMT01 | 375 nm | 1.853353 | 2.750832 | 3.780461 | 4.921091 | 6.019128 | 7.135624 | 8.250303 | 9.312392 | 10.45523 | 11.42943 |
| EMT02 | 395 nm | 1.902312 | 2.315515 | 2.681035 | 2.916676 | 3.171921 | 3.383315 | 3.568757 | 3.795153 | 3.924454 | 4.16658 |
| EMT03 | 468 nm | 1.902312 | 2.315515 | 2.681035 | 2.916676 | 3.171921 | 3.383315 | 3.568757 | 3.795153 | 3.924454 | 4.16658 |
| EMT04 | 574 nm | 1.849806 | 1.94493 | 1.958168 | 2.038014 | 2.073568 | 2.11255 | 2.180982 | 2.166128 | 2.278388 | 2.261538 |
| EMT05 | 595 nm | 1.900876 | 1.907921 | 2.003646 | 2.105552 | 2.105552 | 2.174545 | 2.193022 | 2.298129 | 2.295131 | 2.414173 |
| EMT08 | 630 nm | 1.852596 | 2.048987 | 2.218443 | 2.420598 | 2.621043 | 2.770388 | 3.013623 | 3.148508 | 3.394848 | 3.525919 |
| EMT11 | 700 nm | 1.893634 | 1.933778 | 1.996076 | 2.041263 | 2.034539 | 2.110362 | 2.077323 | 2.1631 | 2.135307 | 2.202237 |
| EMT06 | 810 nm | 1.854301 | 4.918075 | 8.121986 | 11.39953 | 14.66283 | 17.89798 | 21.19421 | 24.38309 | 27.69155 | 30.861 |
| EMT10 | 910 nm | 1.860255 | 3.147739 | 4.804063 | 6.602514 | 8.47922 | 10.29846 | 12.25175 | 14.07092 | 15.98689 | 17.7913 |
| EMT12 | 970 nm | 1.862276 | 2.337754 | 2.849138 | 3.337908 | 3.862763 | 4.288465 | 4.824609 | 5.231804 | 5.724216 | 6.115157 |
| EMT07 | 1200 nm | 1.897568 | 1.872397 | 1.914245 | 1.909906 | 1.912201 | 1.937241 | 1.891351 | 1.967597 | 1.920849 | 1.988393 |
| EMT09 | 1450 nm | 1.896268 | 1.863635 | 1.881641 | 1.876372 | 1.855034 | 1.889938 | 1.833588 | 1.895058 | 1.844704 | 1.902497 |

1% Reduced Fat Milk Scan Data

| | | 0.000000% Level | 11.111111% Level | 22.222222% Level | 33.333333% Level | 44.444444% Level | 55.555556% Level | 66.666667% Level | 77.777778% Level | 88.888889% Level | 100.00000% Level |
|---|---|---|---|---|---|---|---|---|---|---|---|
| DET01 Visible | 380 nm–1100 nm | 0.819594 | 1.240862 | 1.68342 | 2.183992 | 2.650446 | 3.145987 | 3.632719 | 4.109079 | 4.610408 | 5.056012 |
| EMT01 | 375 nm | 0.859433 | 1.846337 | 3.157437 | 4.468596 | 5.825151 | 7.159752 | 8.493031 | 9.832979 | 11.1144 | 12.39506 |
| EMT02 | 395 nm | 0.826049 | 1.424384 | 1.804233 | 2.161086 | 2.448487 | 2.725047 | 2.985627 | 3.21033 | 3.471631 | 3.665954 |
| EMT03 | 468 nm | 0.851417 | 0.883395 | 0.974477 | 1.021934 | 1.092863 | 1.155597 | 1.203561 | 1.279116 | 1.305622 | 1.386837 |
| EMT04 | 574 nm | 0.824708 | 0.912845 | 0.975096 | 1.067662 | 1.137257 | 1.213044 | 1.300383 | 1.344103 | 1.445502 | 1.487851 |
| EMT05 | 595 nm | 0.853294 | 1.045799 | 1.317418 | 1.574123 | 1.83118 | 2.094871 | 2.320767 | 2.606273 | 2.829296 | 3.100443 |
| EMT08 | 630 nm | 0.834423 | 0.945425 | 1.012093 | 1.066989 | 1.127529 | 1.136768 | 1.203835 | 1.211298 | 1.267326 | 1.275826 |
| EMT11 | 700 nm | 0.853819 | 5.513746 | 10.5381 | 15.57565 | 20.63868 | 25.70743 | 30.7491 | 35.8129 | 40.8034 | 45.84657 |
| EMT06 | 810 nm | 0.851512 | 3.027487 | 5.944372 | 9.0823 | 12.30197 | 15.59873 | 18.85341 | 22.15533 | 25.38252 | 28.62325 |
| EMT10 | 910 nm | 0.847888 | 1.67917 | 2.636165 | 3.580869 | 4.47858 | 5.394716 | 6.238401 | 7.116503 | 7.907809 | 8.72506 |
| EMT12 | 970 nm | 0.83009 | 0.87862 | 0.885123 | 0.920683 | 0.93866 | 0.945675 | 0.979519 | 0.96603 | 1.016116 | 1.010311 |
| EMT07 | 1200 nm | 0.851631 | 0.845802 | 0.837648 | 0.842077 | 0.840855 | 0.821757 | 0.84998 | 0.82019 | 0.851631 | 0.827223 |
| EMT09 | 1450 nm | | | | | | | | | | |

2% Reduced Fat Milk Scan Data

| | | 0.000000% Level | 11.111111% Level | 22.222222% Level | 33.333333% Level | 44.444444% Level | 55.555556% Level | 66.666667% Level | 77.777778% Level | 88.888889% Level | 100.00000% Level |
|---|---|---|---|---|---|---|---|---|---|---|---|
| DET01 Visible | 380 nm–1100 nm | 0.570154 | 0.953126 | 1.426524 | 1.900131 | 2.384049 | 2.871317 | 3.349722 | 3.850186 | 4.326171 | 4.814023 |
| EMT01 | 375 nm | 0.56808 | 1.596284 | 2.883786 | 4.229248 | 5.581666 | 6.926287 | 8.28122 | 9.602428 | 10.93705 | 12.17873 |
| EMT02 | 395 nm | 0.570935 | 1.122499 | 1.521474 | 1.85042 | 2.141458 | 2.413941 | 2.65314 | 2.914131 | 3.128863 | 3.35964 |
| EMT03 | 468 nm | 0.557321 | 0.627285 | 0.690264 | 0.756782 | 0.825197 | 0.881302 | 0.957942 | 1.002479 | 1.073146 | 1.115459 |
| EMT04 | 574 nm | 0.566697 | 0.625819 | 0.712556 | 0.793052 | 0.870293 | 0.960738 | 1.026911 | 1.117867 | 1.179367 | 1.263625 |
| EMT05 | 595 nm | 0.559497 | 0.791514 | 1.062191 | 1.337743 | 1.617634 | 1.877785 | 2.167338 | 2.425379 | 2.69894 | 2.951521 |
| EMT08 | 630 nm | 0.566071 | 0.668949 | 0.74898 | 0.817287 | 0.856632 | 0.915468 | 0.940937 | 0.992382 | 1.012451 | 1.046616 |
| EMT11 | 700 nm | 0.56023 | 5.790097 | 11.37227 | 17.00618 | 22.65566 | 28.28727 | 33.94337 | 39.54954 | 45.17048 | 50.73836 |
| EMT06 | 810 nm | 0.562829 | 3.059238 | 6.371916 | 9.933073 | 13.6236 | 17.33267 | 21.078 | 24.78393 | 28.49098 | 32.14504 |
| EMT10 | 910 nm | 0.561607 | 1.571375 | 2.713776 | 3.825009 | 4.934711 | 5.988616 | 7.046408 | 8.042199 | 9.027708 | 9.970004 |
| EMT12 | 970 nm | 0.567591 | 0.594348 | 0.626451 | 0.657058 | 0.672835 | 0.706756 | 0.717986 | 0.755107 | 0.76527 | 0.794995 |
| EMT07 | 1200 nm | 0.570226 | 0.564128 | 0.561845 | 0.56541 | 0.552261 | 0.57019 | 0.557947 | 0.570828 | 0.559568 | 0.572038 |
| EMT09 | 1450 nm | | | | | | | | | | |

Whole Milk Scan Data

| | | 0.000000% Level | 11.111111% Level | 22.222222% Level | 33.333333% Level | 44.444444% Level | 55.555556% Level | 66.666667% Level | 77.777778% Level | 88.888889% Level | 100.00000% Level |
|---|---|---|---|---|---|---|---|---|---|---|---|
| DET01 Visible | 380 nm–1100 nm | | | | | | | | | | |

-continued

| | | | | | | | | | |
|---|---|---|---|---|---|---|---|---|---|
| EMT01 | 375 nm | 0.16641 | 0.596839 | 1.095736 | 1.623416 | 2.144379 | 2.67843 | 3.204668 | 3.740919 | 4.264611 | 4.780668 |
| EMT02 | 395 nm | 0.180167 | 1.260585 | 2.648545 | 4.075349 | 5.526269 | 6.96534 | 8.407713 | 9.834225 | 11.25157 | 12.59331 |
| EMT03 | 468 nm | 0.166142 | 0.772774 | 1.188403 | 1.550609 | 1.86072 | 2.156073 | 2.422726 | 2.685619 | 2.93147 | 3.162682 |
| EMT04 | 574 nm | 0.168383 | 0.224215 | 0.306702 | 0.376278 | 0.454354 | 0.519794 | 0.591284 | 0.656432 | 0.716335 | 0.774854 |
| EMT05 | 595 nm | 0.162995 | 0.240982 | 0.325096 | 0.421572 | 0.505304 | 0.599819 | 0.685155 | 0.767303 | 0.848723 | 0.921691 |
| EMT08 | 630 nm | 0.170296 | 0.405359 | 0.706476 | 1.00627 | 1.306892 | 1.595658 | 1.889521 | 2.183604 | 2.463085 | 2.7484 |
| EMT11 | 700 nm | 0.16551 | 0.28764 | 0.372332 | 0.448513 | 0.505787 | 0.552481 | 0.596148 | 0.631243 | 0.671303 | 0.695062 |
| EMT06 | 810 nm | 0.171459 | 6.009889 | 12.26236 | 18.56036 | 24.89096 | 31.20731 | 37.51296 | 43.81593 | 50.09204 | 56.34823 |
| EMT10 | 910 nm | 0.171655 | 3.01565 | 6.805504 | 10.88362 | 15.09146 | 19.34855 | 23.61964 | 27.87355 | 32.0931 | 36.27593 |
| EMT12 | 970 nm | 0.170881 | 1.365978 | 2.723706 | 4.059857 | 5.36235 | 6.630171 | 7.866824 | 9.07215 | 10.2319 | 11.36832 |
| EMT07 | 1200 nm | 0.163513 | 0.20923 | 0.239235 | 0.282758 | 0.308281 | 0.340474 | 0.366426 | 0.391942 | 0.417328 | 0.435591 |
| EMT09 | 1450 nm | 0.163263 | 0.170827 | 0.166452 | 0.172919 | 0.167078 | 0.16982 | 0.173622 | 0.167376 | 0.171256 | 0.167787 |

The preliminary data indicate that the ChromaID technology can be used for the quality control and monitoring of dairy products, in particular, milk products. To reduce the cost and simplify the production of the instrument, that is a ChromaID Scanner, in one embodiment, the scan head may be redesigned to include only five emitters: EMT 01, 06, 10, 11 and 12 and their corresponding photodiodes sensors with sensing capability at 355 nm, 700 nm, 810 nm, 910 nm, and 970 nm. Such a scan head can be significantly miniaturized due to the extra space liberated by the reduced numbers of emitters needed and photodiodes. The configuration of such a new scan head could basically adopt the existing scan head technology. These LEDs were found to provide the most discriminating data for dairy products, as shown by the tabular chromatic profile data. For the in-line monitoring of dairy products, the scan head could be built directly into a diary product production line and provide a continuous monitoring on the diary product. Chromatic profiles would be generated as the products passed by the scanner head, and compared using a computer coupled to a database of reference scans. An alarm or other form of signal could be generated if any of the product samples produced chromatic profiles that varied significantly from the reference.

Figure 7:
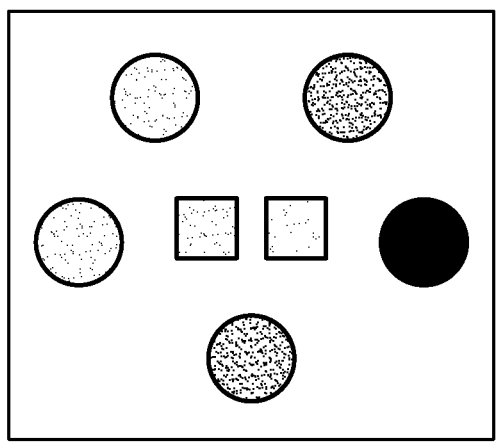
FIG. 7 shows a chromatic scanner head with 5 LEDs and 2 photodetectors according to one embodiment.

Alternatively, for end-consumer applications, a scan head could be miniaturized into a scanner head that was configured to couple (through wire or wireless coupling) to a personal device, like a smart cellular phone, a laptop, a tablet, and so on The personal computing device would have an APP designed to run the scanning operation, accept the data input, access database reference standards and prepare a report on the product being tested. One embodiment of a miniaturized scanner head is shown in FIG. 7. The illustrated embodiment has five emitters (corresponding to EMTs 01, 06, 10, 11 and 12 and photodiode photodetectors configured to detect at least reflected light in the wavelengths of 355 nm, 700 nm, 810 nm, 910 nm, and 970 nm.

Figure 8:
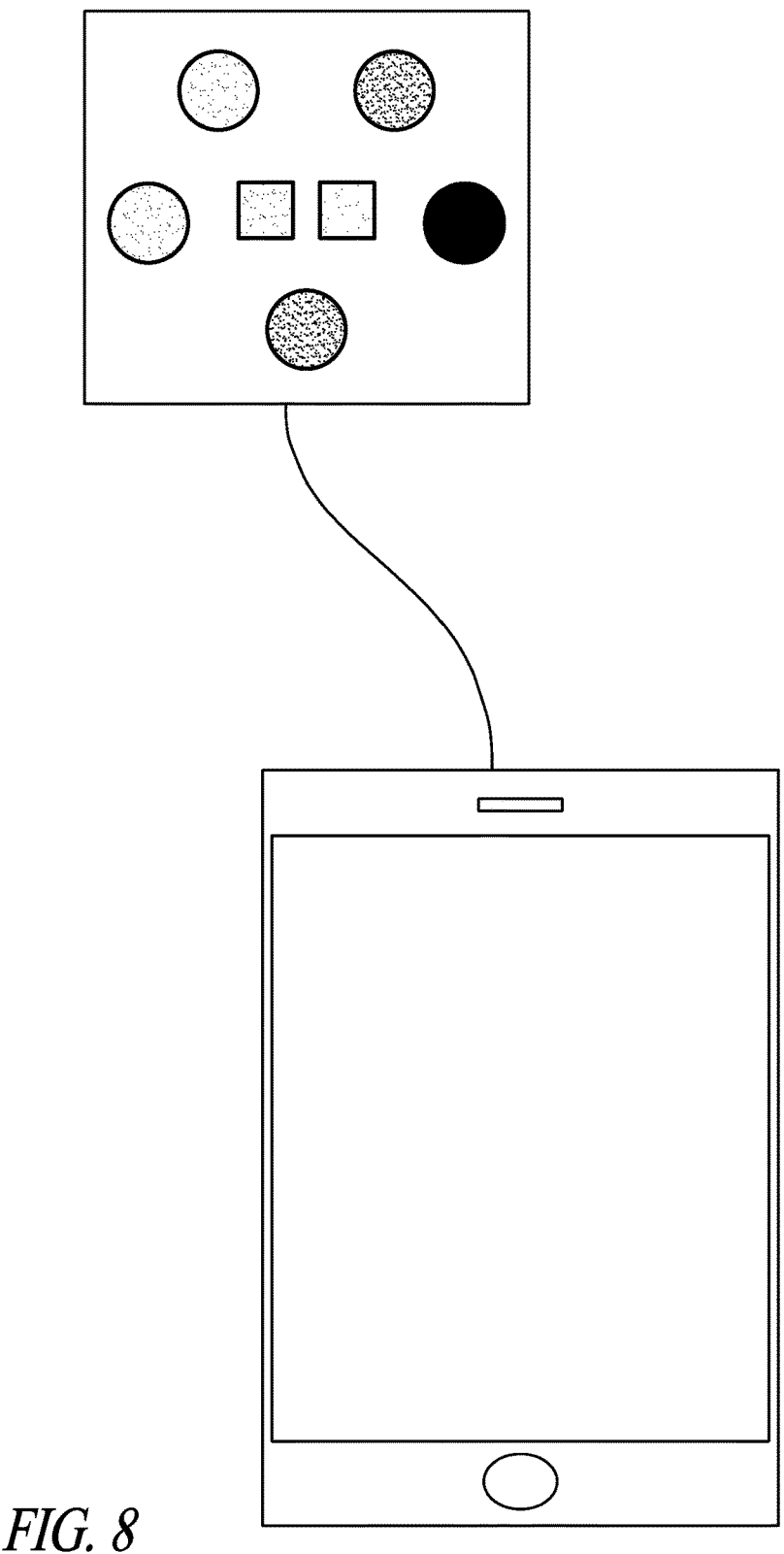
FIG. 8 shows the chromatic scanner head of FIG. 7, coupled to a smart phone according to one embodiment.
Figure 9:
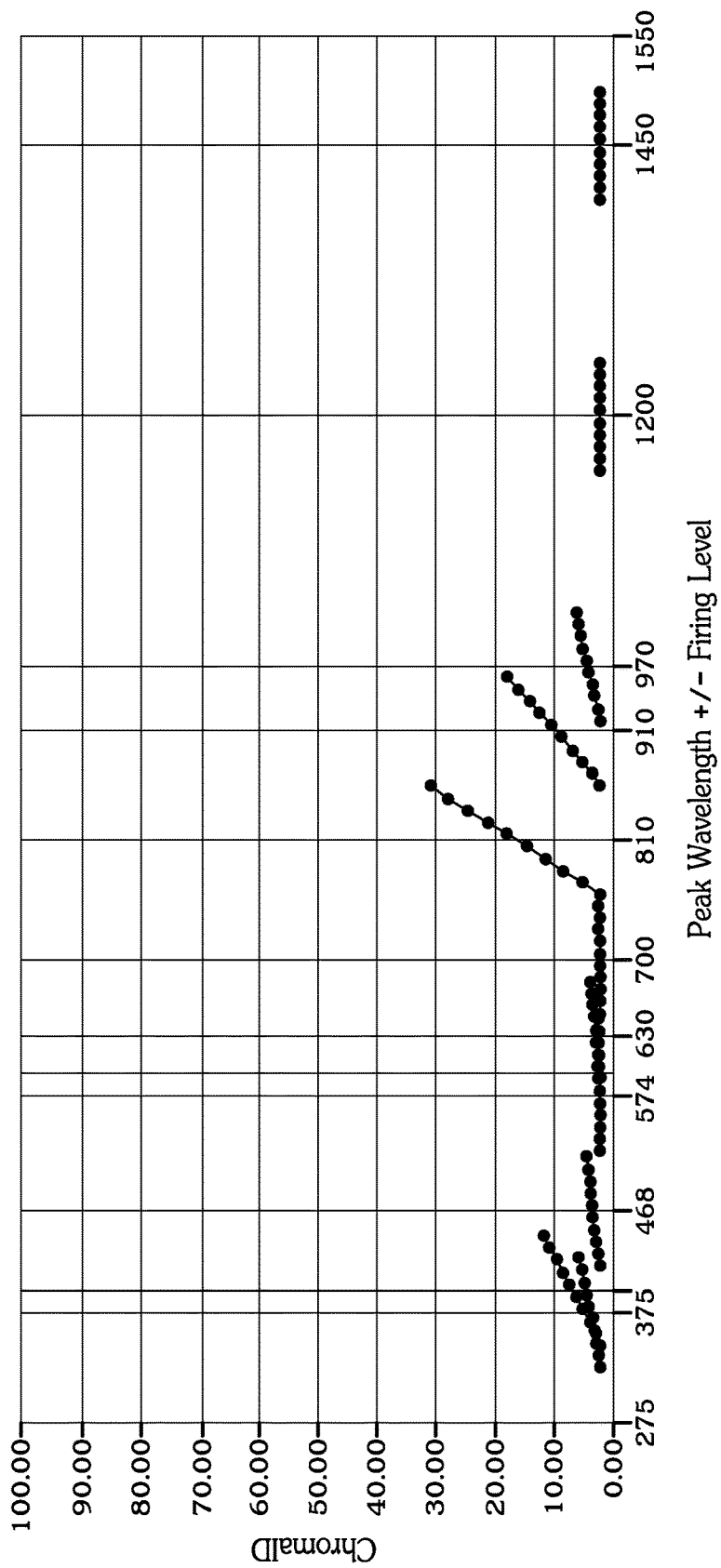
FIG. 9 is a chromatic scan profile for skim milk.
Figure 10:
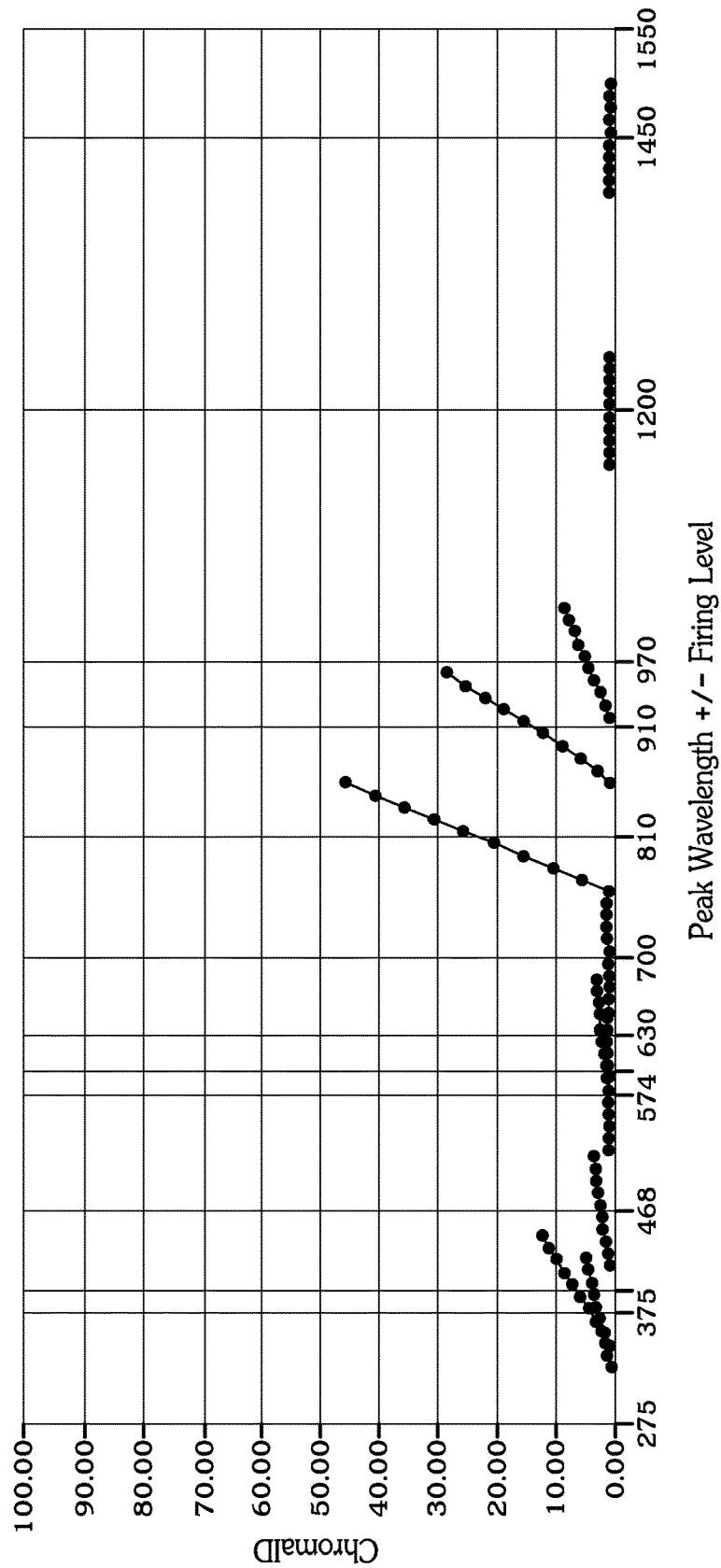
FIG. 10 is a chromatic scan profile for 1% reduced fat milk.
Figure 11:
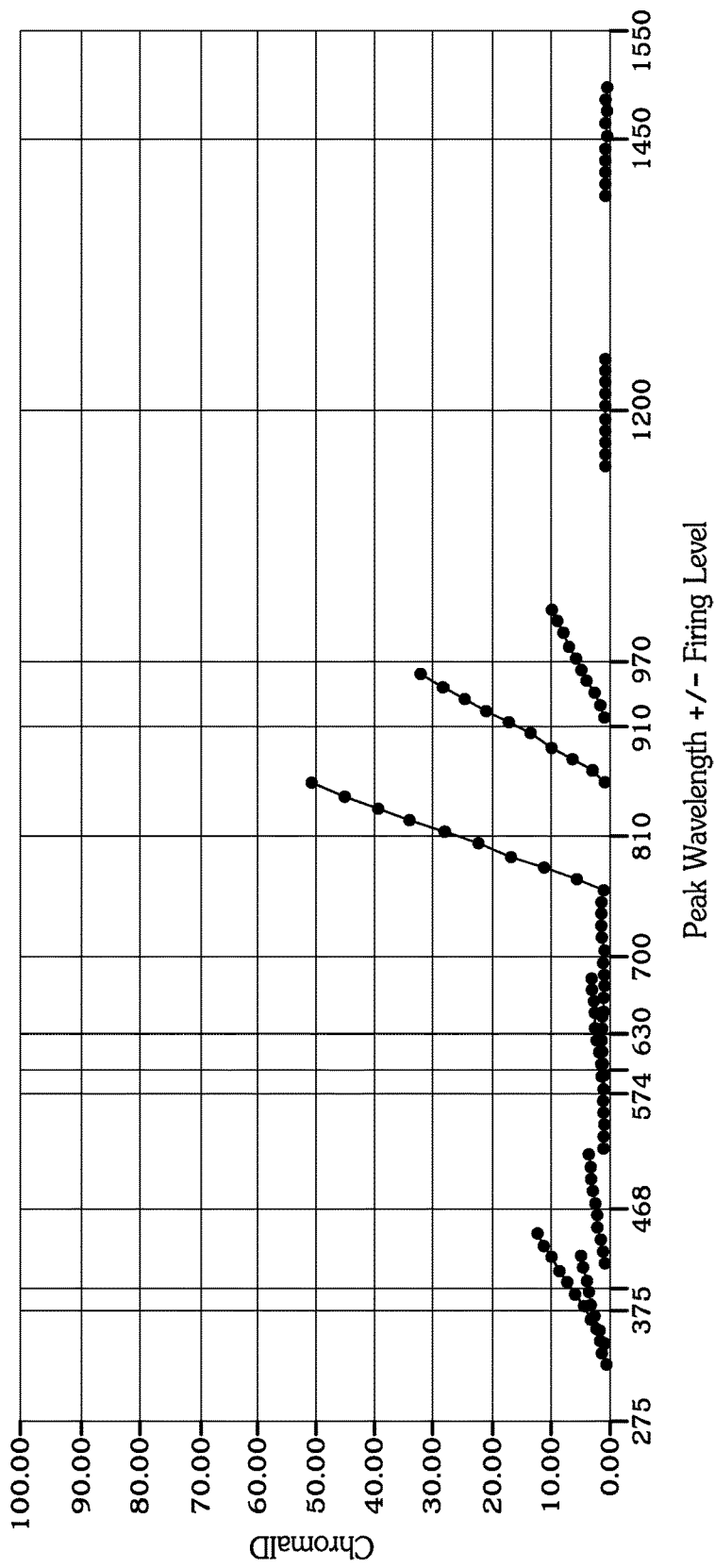
FIG. 11 is a chromatic scan profile for 2% reduced fat milk.
Figure 12:
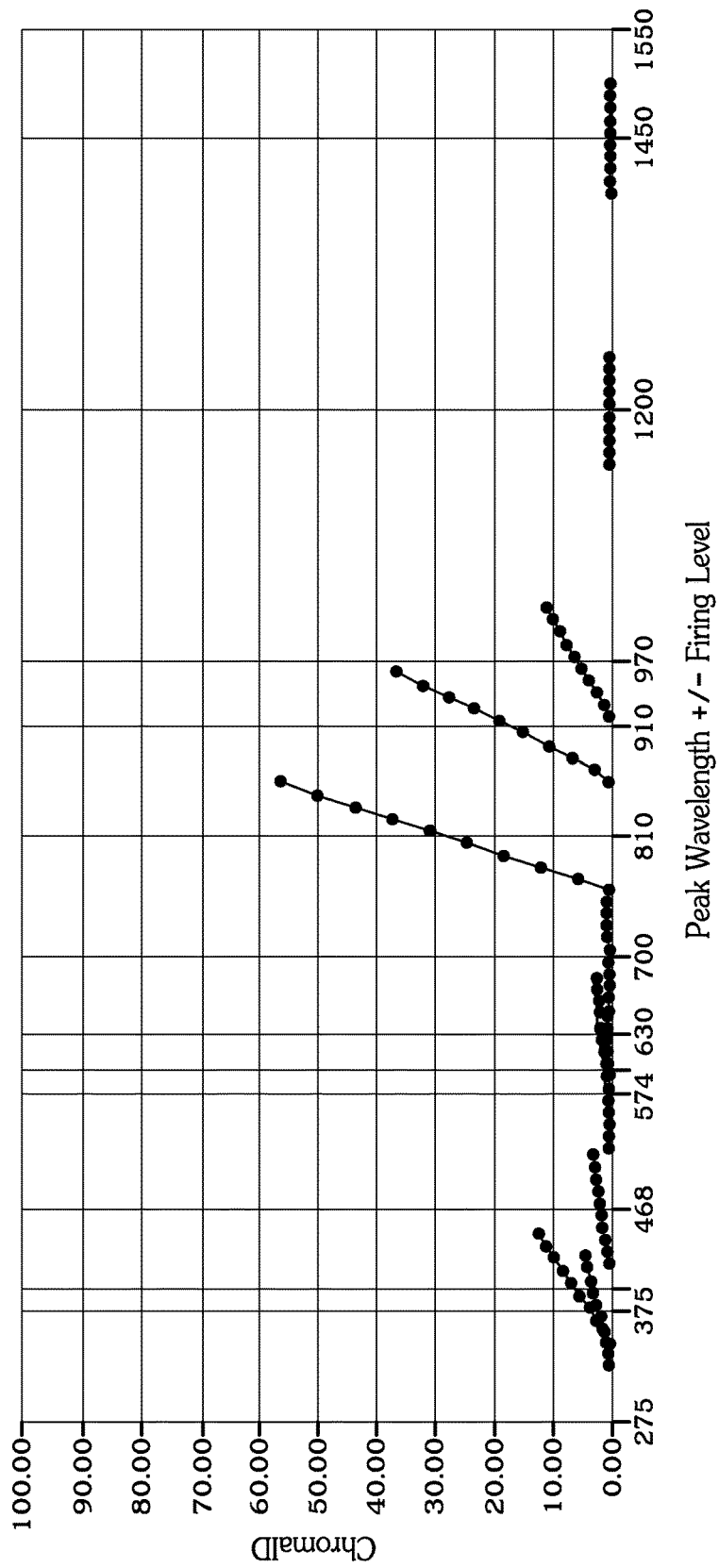
FIG. 12 is a chromatic scan profile for whole milk.

The miniaturized consumer scan head could be a "dumb" scan head with no controller or programming. It may plug into a mobile phone jack. The software that is running the scan head could be an APP in the mobile phone. Similar, the scan head could draw energy from the battery source of the phone (FIG. 8). The running of the scan head is controlled through the APP and the result is displayed on the mobile phone. The APP may allow a user to run the scan on a diary product for information, such as production, nutritional facts, and so on The APP may contain a database of ChromaID data on dairy products. The scan carried out by the consumers could be compared to the database data and the APP could provide a verification or identification on a product the consumer is scanning In some examples, an apparatus for evaluating a food product, such as a dairy product, comprises a chromatic scanner system, the system comprising a scanner head comprising a plurality of light sources, each light source configured to emit light of a different interrogation wavelength, and one or more photodetectors, each configured to detect an intensity of reflected or otherwise returned light from a sample when the sample is illuminated with light from each of the different interrogation wavelengths. The illumination may include sequential illumination of each of the light sources. The one or more photodetectors may be configured to generate a signal corresponding to the intensity of reflected light. The system may further comprise a controller operably coupled to the scanner head, and configured to activate the one or more light sources in accordance with a sequential pattern, receive the corresponding signals from the one or more photodetectors, and generate a spectral pattern of reflected light intensities as a function of interrogation wavelength.

In some examples, a method for evaluating a food product, such as a dairy product, comprises scanning a surface of a dairy product test sample to generate a spectral pattern from the test sample and comparing the spectral pattern from the test sample with reference spectral patterns from one or more reference food products, such as reference dairy products. In some example, the spectral pattern may be evaluated for the level (e.g. concentration such as weight or volume percentage) of a food component, such as fat, protein, water, and the like. In some examples, the spectral pattern may be evaluated for a degree of aging. For example, reference spectral patterns may be obtained from cheese or other food product as a function of aging. In some examples, reference spectral patterns may be obtained from cheese, milk, or other food product as a function of aging In some examples, a dairy product may be a food product formed using milk obtained from a mammal, such as a cow, goat, buffalo, horses, and the like. A dairy product may comprise one or more of: cream (such as single cream, double cream, whipping cream, sour cream, fermented cream, and the like), butter (including clarified butter), buttermilk, milk (such as whole milk, condensed milk, evaporated milk, skim milk, high fat milk, fermented milk, and the like), powdered milk (such as dried milk powder), whey (including acidified whey), curds, cheese (such as ricotta, cottage cheese, cheddar, and the like), milk fat, clarified butter, casein (such as sodium or calcium caseinate, food products including casein or other milk proteins), artificial creamers (e.g. including milk products such as casein and its derivatives), milk protein, whey protein, yoghurt (such as frozen yoghurt), ice cream, gelato, custard (such as frozen custard), and the like. Spectral data may be used to determine the levels (e.g. concentration by weight and/or volume) of one or more of the following: milk fat, milk protein, milk sugars, ice, water, additives (such as sugar, color, and/or flavor), the presence of bacteria and/or bacterial products, and the like.

In some examples, a system may include additional functionality, such as a bar code reader or other mechanism to identify a food sample, individual animal, operator, or other information associated with the spectral data. An apparatus may further comprise the functionality of a flashlight, camera, sterilizer (e.g. including at least one UV light source capable of removing bacteria and/or other pathogens), GPS data and/or other location device.

In some examples, a ratio of fat to protein levels (e.g. concentration ratio, by weight and/or volume) may be determined. In some examples, counterfeit products may be detected, e.g. low fat milk with non-milk fat added, by comparison to reference spectral data corresponding to genuine and counterfeit examples.

In some examples, reference data are collected from a variety of food product samples, such as milk with a range of milk fat concentrations, cheese with a variety of fat and/or protein concentrations, cheese as a function of age, cheese as a function of taste (for example, using blind taste test data, for example aged cheeses as a function of taste), and the like.

In some examples, light emission peak wavelength from a light source such as an LED may be adjusted as a function of an applied electrical current, voltage signal, and the like. Hence, the interrogation wavelength may be adjusted for a single light source, such as a single LED, allowing different interrogation wavelengths to be obtained from a single light source. In some examples, light emission data may be collected from a reference reflector and used to normalize spectral data. In some examples, an apparatus may be in wireless communication with a network, allowing retrieval of reference spectral data.

With respect to the use of substantially any plural and/or singular terms herein, those having skill in the art can translate from the plural to the singular and/or from the singular to volume of wastewater can be received in the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," and so on). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, and so on" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, and so on). In those instances where a convention analogous to "at least one of A, B, or C, and so on" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, and so on). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and so on As a non-limiting example, each range discussed herein can be readily broken down into a lower third, middle third and upper third, and so on As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

What is claimed is:

1. A method for quality control of dairy products, the method comprising:
   providing a chromatic scanner system, comprising:
      a scanner head comprising one or more light sources, wherein each light source is configured to emit light of a different interrogation wavelength, and one or more photodetectors, wherein each photodetector is configured to detect an intensity of reflected light for each of the different interrogation wavelengths, and wherein the one or more photodetectors are further configured to generate signals corresponding to the intensity of reflected light; and
      a controller operably coupled to the scanner head, wherein the controller is configured to activate the one or more light sources in accordance with a sequential pattern, wherein varying the sequential pattern produces an encryption of the corresponding signals indicative of a dairy product test sample, receive the corresponding signals from the one or more photodetectors, and generate a spectral pattern of reflected light intensities;
   scanning a surface of the dairy product test sample to generate a spectral pattern unique to the dairy product test sample; and
   comparing the spectral pattern from the dairy product test sample with spectral patterns from one or more reference dairy products.

2. The method of claim 1, wherein the one or more light sources are light emitting diodes (LEDs).

3. The method of claim 2, wherein the scanner head comprises 1 to 20 LEDs.

4. The method of claim 2, wherein the scanner head comprises at least 5 LEDs.

5. The method of claim 4, wherein the at least 5 LEDs emit light in ultraviolet (UV), visible, and infrared (IR) wavelengths.

6. The method of claim 1, wherein the one or more photodetectors include photodiodes.

7. The method of claim 1, wherein the scanner head comprises 1 to 20 photodiode detectors.

8. The method of claim 1, wherein the scanner head comprises 1, 2, 3, 4, or 5 photodiode detectors.

9. The method of claim 8, wherein the 1, 2, 3, 4, or 5 photodiode detectors in the scanner head detect reflected light at wavelengths selected from 355 nm, 700 nm, 810 nm, 910 nm, and 970 nm.

10. The method of claim 1, further comprising positioning at least one of the one or more light sources and the one or more photodetectors in the scanner head at a distance of about 0.1 cm to 10 cm from the surface of the dairy product test sample.

11. The method of claim 10, wherein the distance is about 1 cm.

12. The method of claim 10, wherein the at least one of the one or more light sources and the one or more photodetectors are positioned substantially normal to the surface of the dairy product test sample.

13. The method of claim 1, wherein the controller is a computer or a smart phone.

14. The method of claim 13, wherein the smart phone comprises an APP configured to run the scanning and comparing operations.

15. The method of claim 1, further comprising verifying or identifying the dairy product test sample based on the comparison of the spectral patterns.

16. The method of claim 1, wherein the chromatic scanner system is configured for continuous scanning and comparing to provide quality control on a production line.

17. The method of claim 1, further comprising determining nutritional information based on the comparison of the spectral patterns.

18. The method of claim 17, wherein the nutritional information comprises fat and protein content.

19. The method of claim 1, wherein the spectral patterns from the one or more reference dairy products are generated before or after the spectral patterns from the dairy product test sample.

20. The method of claim 1, wherein the spectral patterns from the one or more reference dairy products are previously generated and stored in a database accessible by the controller.

21. The method of claim 20, wherein the database is stored on a memory device directly coupled to the controller.

22. The method of claim 20, wherein the database is accessible on-line or via cellular communication.

23. A chromatic scanner system for quality control of dairy products, the chromatic scanner system comprising:

a scanner head comprising light emitting diodes (LEDs) and a photodetector, wherein each LED is configured to emit light of a different interrogation wavelength, and wherein the LEDs comprise a UV LED, a visible LED, and a near-IR LED, wherein the photodetector is configured to detect an intensity of reflected light for each of the different interrogation wavelengths, and wherein the photodetector is further configured to generate a signal corresponding to the intensity of reflected light; and a controller operably coupled to the scanner head, wherein the controller is configured to activate the LEDs in accordance with a predetermined sequential pattern, wherein varying the predetermined sequential pattern produces an encryption of the corresponding signal indicative of a dairy product test sample, receive the corresponding signal from the photodetector, and generate a spectral pattern of reflected light intensities;

wherein the controller comprises an operable coupling for accessing spectral patterns from a plurality of dairy products stored on a database accessible to the controller through the operable coupling.

24. The chromatic scanner system of claim 23, wherein the controller is a computer or a smart phone.

25. The chromatic scanner system of claim 23, further comprising a positioning guide coupled to the scanner head, wherein the positioning guide facilitates positioning at a standard distance and light incidence angle.

26. The chromatic scanner system of claim 23, further comprising a hood to limit interference from environmental light with the generation of the spectral pattern.

27. The chromatic scanner system of claim 23, further comprising optical components selected from collimators, lenses, filters, beam splitters, amplifiers, and optical fibers.

* * * * *